US012672946B2

(12) United States Patent
Chen et al.

(10) Patent No.: US 12,672,946 B2
(45) **Date of Patent: \*Jul. 7, 2026**

(54) METHOD OF MAKING SEMICONDUCTOR DEVICE WHICH INCLUDES FINS

(71) Applicant: TAIWAN SEMICONDUCTOR MANUFACTURING COMPANY, LTD., Hsinchu (TW)

(72) Inventors: Chih-Liang Chen, Hsinchu (TW); Chih-Ming Lai, Hsinchu (TW); Charles Chew-Yuen Young, Hsinchu (TW); Chin-Yuan Tseng, Hsinchu (TW); Jiann-Tyng Tzeng, Hsinchu (TW); Kam-Tou Sio, Hsinchu (TW); Ru-Gun Liu, Hsinchu (TW); Wei-Liang Lin, Hsinchu (TW); L. C. Chou, Hsinchu (TW)

(73) Assignee: TAIWAN SEMICONDUCTOR MANUFACTURING COMPANY, LTD., Hsinchu (TW)

( * ) Notice: Subject to any disclaimer, the term of this patent is extended or adjusted under 35 U.S.C. 154(b) by 615 days.

This patent is subject to a terminal disclaimer.

(21) Appl. No.: 18/190,670

(22) Filed: Mar. 27, 2023

(65) Prior Publication Data

US 2023/0247817 A1      Aug. 3, 2023

Related U.S. Application Data

(60) Continuation of application No. 17/552,433, filed on Dec. 16, 2021, now Pat. No. 11,616,067, which is a (Continued)

(51) Int. Cl.
    *H10B 10/00*          (2023.01)
    *A61B 5/00*           (2006.01)
                    (Continued)

(52) U.S. Cl.
    CPC .......... *A61C 19/045* (2013.01); *A61B 5/0077* (2013.01); *A61B 5/0088* (2013.01); *A61B 5/1127* (2013.01); *A61B 5/682* (2013.01); *A61B 34/20* (2016.02); *A61B 90/39* (2016.02); *H10B 10/12* (2023.02); *H10D 30/024* (2025.01); *H10D 30/6211* (2025.01);
                    (Continued)

(58) Field of Classification Search
    CPC .. H10B 10/12; A81C 19/045; H10D 30/6211; H10D 84/0158; H10D 84/834; H10D 84/038
    See application file for complete search history.

(56) References Cited

U.S. PATENT DOCUMENTS 8,617,996 B1    12/2013  Chi et al.
9,257,439 B2    2/2016   Liaw
                    (Continued)

*Primary Examiner* — Nathan W Ha
(74) *Attorney, Agent, or Firm* — Hauptman Ham, LLP

(57)          ABSTRACT

A method (of manufacturing fins for a semiconductor device) includes: forming semiconductor fins including ones thereof having a first cap with a first etch sensitivity (first capped fins) and second ones thereof having a second cap with a second etch sensitivity (second capped fins), the first and second etch sensitivities being different; and eliminating selected ones of the first capped fins and selected ones of the second capped fins.

20 Claims, 24 Drawing Sheets

Related U.S. Application Data continuation of application No. 16/918,798, filed on Jul. 1, 2020, now Pat. No. 11,222,899, which is a continuation of application No. 16/126,875, filed on Sep. 10, 2018, now Pat. No. 10,714,485, which is a division of application No. 15/362,002, filed on Nov. 28, 2016, now Pat. No. 10,074,657.

(60) Provisional application No. 62/328,837, filed on Apr. 28, 2016.

(51) Int. Cl.

| | | |
|---|---|---|
| *A61B 5/11* | (2006.01) | |
| *A61B 34/20* | (2016.01) | |
| *A61B 90/00* | (2016.01) | |
| *A61C 19/045* | (2006.01) | |
| *H10D 30/01* | (2025.01) | |
| *H10D 30/62* | (2025.01) | |
| *H10D 84/01* | (2025.01) | |
| *H10D 84/03* | (2025.01) | |
| *H10D 84/83* | (2025.01) | |
| *H10P 50/00* | (2026.01) | |

(52) U.S. Cl.

CPC ....... *H10D 84/0158* (2025.01); *H10D 84/038* (2025.01); *H10D 84/834* (2025.01); *H10P 50/693* (2026.01); *H10P 50/695* (2026.01); *A61B 2034/2055* (2016.02); *A61B 2034/2065* (2016.02); *A61B 2090/3945* (2016.02); *A61B 2090/3983* (2016.02); *A61B 2090/3991* (2016.02); *A61B 2560/0223* (2013.01); *H10P 50/73* (2026.01)

(56) References Cited

U.S. PATENT DOCUMENTS

| | | | |
|---|---|---|---|
| 9,691,775 B1 | 6/2017 | Licausi | |
| 9,734,897 B1 | 8/2017 | Zang | |
| 9,735,054 B2 | 8/2017 | Fan | |
| 9,761,452 B1 | 9/2017 | Shu | |
| 10,074,657 B2 * | 9/2018 | Chen | H10D 84/0158 |
| 10,714,485 B2 * | 7/2020 | Chen | H01L 21/3086 |
| 2006/0068531 A1 | 3/2006 | Breitwisch | |
| 2007/0267676 A1 * | 11/2007 | Kim | H10D 30/024 |
| | | | 257/E21.429 |
| 2007/0287255 A1 * | 12/2007 | Doyle | H10D 30/024 |
| | | | 438/283 |
| 2008/0003833 A1 * | 1/2008 | Kim | H10B 12/053 |
| | | | 257/E21.409 |
| 2008/0308848 A1 | 12/2008 | Inaba | |
| 2009/0179193 A1 | 7/2009 | Appenzeller | |
| 2010/0197141 A1 | 8/2010 | Tu | |
| 2013/0082333 A1 | 4/2013 | Chen et al. | |
| 2013/0196508 A1 * | 8/2013 | Licausi | H10D 84/0193 |
| | | | 438/696 |
| 2013/0292777 A1 | 11/2013 | Liaw | |
| 2013/0330889 A1 | 12/2013 | Mn et al. | |
| 2015/0041812 A1 | 2/2015 | Cheng | |
| 2015/0091097 A1 | 4/2015 | Wu | |
| 2015/0108851 A1 | 4/2015 | Shieh et al. | |
| 2015/0111362 A1 | 4/2015 | Shieh et al. | |
| 2015/0206954 A1 * | 7/2015 | Lin | H10D 30/024 |
| | | | 257/365 |
| 2015/0249127 A1 | 9/2015 | Xie et al. | |
| 2015/0294976 A1 * | 10/2015 | Kim | H01L 21/3086 |
| | | | 438/702 |
| 2015/0311337 A1 | 10/2015 | Cai et al. | |
| 2016/0043225 A1 | 2/2016 | Ching et al. | |
| 2016/0071730 A1 | 3/2016 | Tung et al. | |
| 2016/0197079 A1 | 7/2016 | Lin et al. | |
| 2016/0211168 A1 * | 7/2016 | Paak | H10B 41/44 |
| 2016/0218010 A1 * | 7/2016 | Lee | H10B 10/12 |
| 2016/0307803 A1 | 10/2016 | Mun et al. | |
| 2016/0315085 A1 | 10/2016 | Choi et al. | |
| 2016/0315147 A1 | 10/2016 | Leobandung et al. | |
| 2016/0372476 A1 * | 12/2016 | Hung | H10D 30/6211 |
| 2017/0005102 A1 * | 1/2017 | Feng | H10D 84/0128 |
| 2017/0069504 A1 * | 3/2017 | Li | H01L 21/461 |
| 2017/0170174 A1 | 6/2017 | Chang | |

* cited by examiner

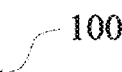
100

104 form a structure including a semiconductor substrate and capped semiconductor fins organized into at least first and second subsets thereof;

wherein:

each member of the first subset has a first cap with a first etch sensitivity (ES1);

each member of the second subset has a second cap with a second etch sensitivity (ES2); and $ES1 \neq ES2$

106 eliminate selected members of the first set and selected members of the second set from the structure

110 selectively remove the second caps of undesired members of the second set to form second uncapped fins

112 selectively remove the first caps of undesired members of the first set to form first uncapped fins

114 at least substantially remove the first and second uncapped fins from the structure

108 form remainder of semiconductor device

FIG. 1

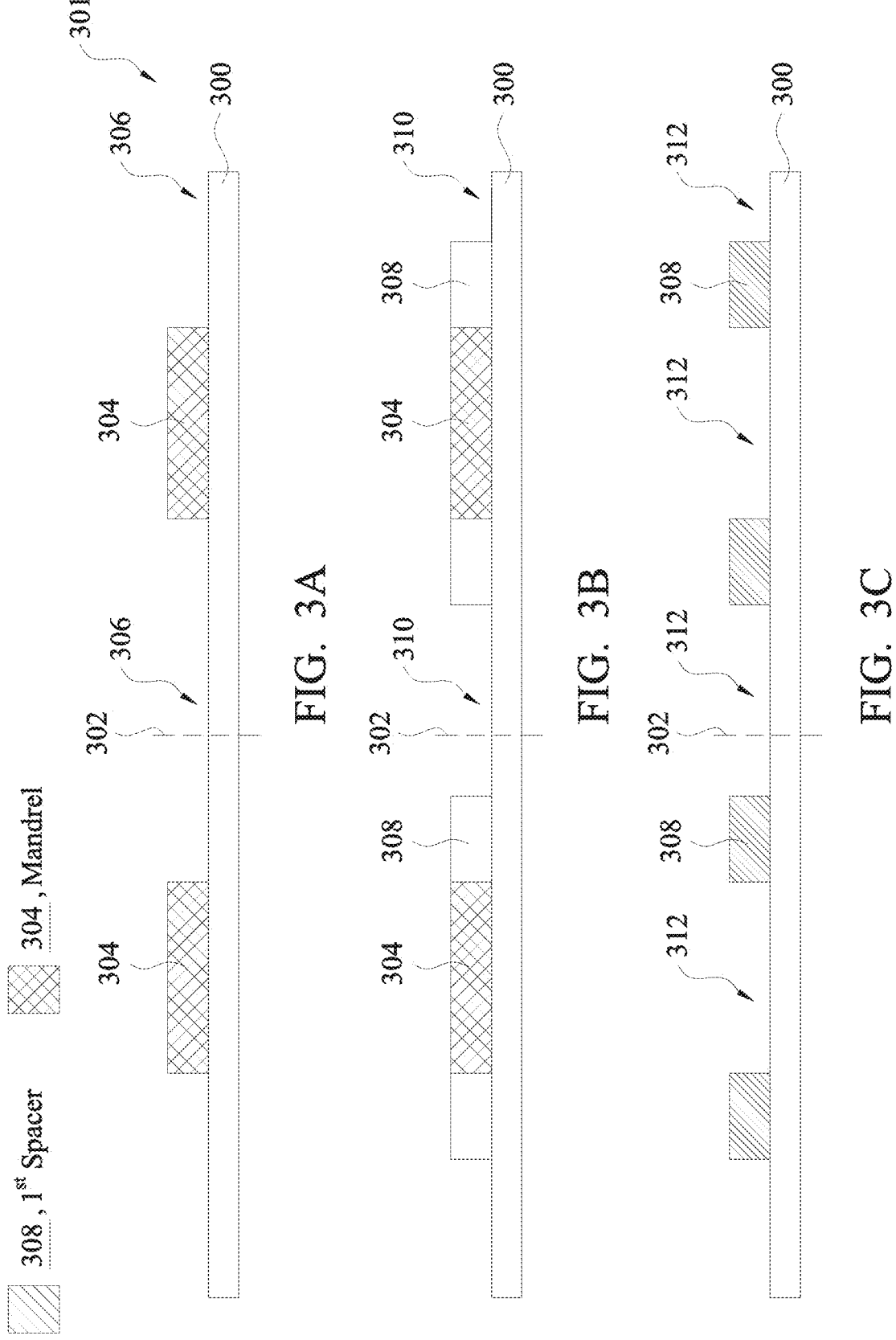

METHOD OF MAKING SEMICONDUCTOR DEVICE WHICH INCLUDES FINS

PRIORITY CLAIM

The present application is a continuation of U.S. application Ser. No. 17/552,433, filed Dec. 16, 2021, now U.S. Pat. No. 11,616,067, issued Mar. 28, 2023, which is a continuation of U.S. application Ser. No. 16/918,798, filed Jul. 1, 2020, now U.S. Pat. No. 11,222,899, issued Jan. 11, 2022, which is a continuation of U.S. application Ser. No. 16/126,875, filed Sep. 10, 2018, now U.S. Pat. No. 10,714, 485, issued Jul. 14, 2020, which is a divisional of U.S. application Ser. No. 15/362,002, filed Nov. 28, 2016, now U.S. Pat. No. 10,074,657, issued Sep. 11, 2018, which claims the priority of U.S. Provisional Application No. 62/328,834, filed Apr. 28, 2016, which are incorporated herein by reference in their entireties.

BACKGROUND

The semiconductor integrated circuit (IC) industry has experienced rapid growth. In the course of IC evolution, functional density (the number of interconnected devices per chip area) has generally increased while geometry size (the smallest component (or line) that can be created using a fabrication process) has decreased. In addition to providing benefits, this scaling down process has increased the complexity of processing and manufacturing ICs.

Logic circuits and embedded static random-access memory (SRAM) cells are frequently integrated into semiconductor devices for increased functional density. To meet the demand for higher SRAM density, simply scaling down the semiconductor feature size is no longer enough. For example, traditional SRAM cell structure with planar transistors has experienced degraded device performance and higher leakage when manufactured with smaller semiconductor geometries. One of the techniques for meeting such a challenge is to use three-dimensional transistors having a fin or multi-fin structure (e.g., Fin-FETs). To improve short channel control and area reduction, the fin structures are desired to be as thin as possible. One of the techniques for manufacturing thin fin structures is spacer lithography. For example, spacers are built on sidewalls of mandrel patterns. After the mandrel patterns are removed, the spacers become an etch mask for etching a silicon substrate in forming the fin structures. The dimensions of the mandrel patterns and spacers control the width and pitch of the fin structures. A tight control of critical dimension (CD) uniformity of the mandrel patterns and spacers is a design challenge for embedded Fin-FET SRAM.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. Moreover, the dimensions of the various features may be arbitrarily increased or reduced for clarity of discussion.

FIG. 1 is a flowchart of a method 100 of manufacturing fins for a semiconductor device which includes Fin-FETs in accordance with at least one embodiment of the present disclosure.

DETAILED DESCRIPTION

Figures 2A, 2B:
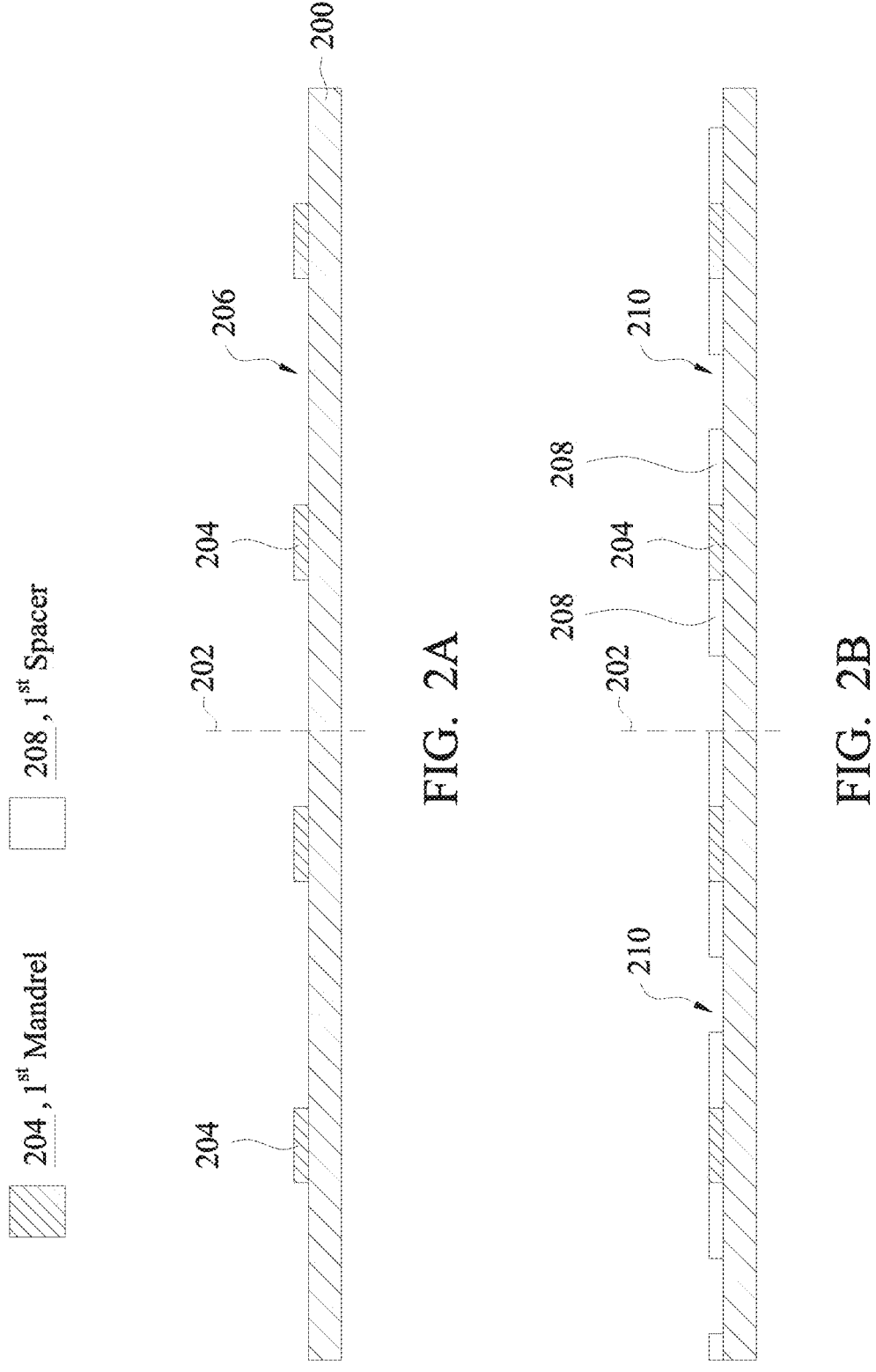
FIGS. 2A-2S are cross-sections of various stages in the manufacture of fins for a semiconductor device which includes Fin-FETs in accordance with at least one embodiment of the present disclosure.

The following disclosure provides many different embodiments, or examples, for implementing different features of the provided subject matter. Specific examples of components, materials, values, steps, arrangements or the like are described below to simplify the present disclosure. These are, of course, merely examples and are not intended to be limiting. Other components, materials, values, steps, arrangements or the like are contemplated. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. The term mask, photolithographic mask, photomask and reticle are used to refer to the same item.

The present disclosure, in various embodiments, is generally related to using spacer techniques to reduce variation in the fin-thickness, $T_{Si}$, of fins for a semiconductor device. Semiconductor devices which include Fin-FETs exhibit variations in fin-thickness $T_{Si}$. With the present disclosure, the variation of $T_{Si}$ in semiconductor devices is reduced by up to about 30%. Further, semiconductor devices which include Fin-FETs exhibit variations in fin-thickness $T_{Si}$ of significantly less than about 50%, e.g., about 20%. As such, with the present disclosure, for any two instances of fins, a thickness of the first fin will vary with respect to the second fin by significantly less than about 50%, e.g., by less than up to about 20%.

In some embodiments, masking techniques (whose relative edge-alignment inaccuracy otherwise could not produce fins having a desired fin-pitch while also exhibiting $T_{Si}$ of significantly less than about 50%) are combined with interleaved fin-caps of different etch selectivity. Use of the interleaved fin-caps of different etch selectivity, in effect, reduces (if not eliminates) the problems otherwise introduced by the edge-alignment inaccuracy of the masking techniques.

FIG. 1 is a flowchart of a method 100 of manufacturing fins for a semiconductor device which includes Fin-FETs in accordance with at least one embodiment of the present disclosure. Additional operations can be provided before, during, and after the method 100.

In FIG. 1, at a block 104, a structure (e.g., an intermediate structure 239 of FIG. 2L or intermediate structure 341 of FIG. 3P) is formed which includes a semiconductor substrate and a plurality of capped semiconductor fins. In some embodiments, the plurality of capped semiconductor fins is organized into at least first and second sets of capped semiconductor fins. Each member of the first set has a first cap with a first etch sensitivity, $ES_{CAP1}$. Each member of the second set has a second cap with a second etch sensitivity, $ES_{CAP2}$, the second etch sensitivity being different than the first etch sensitivity, $ES_{CAP2} \neq ES_{CAP1}$. From block 104, flow proceeds to a block 106.

Figures 2C, 2D:
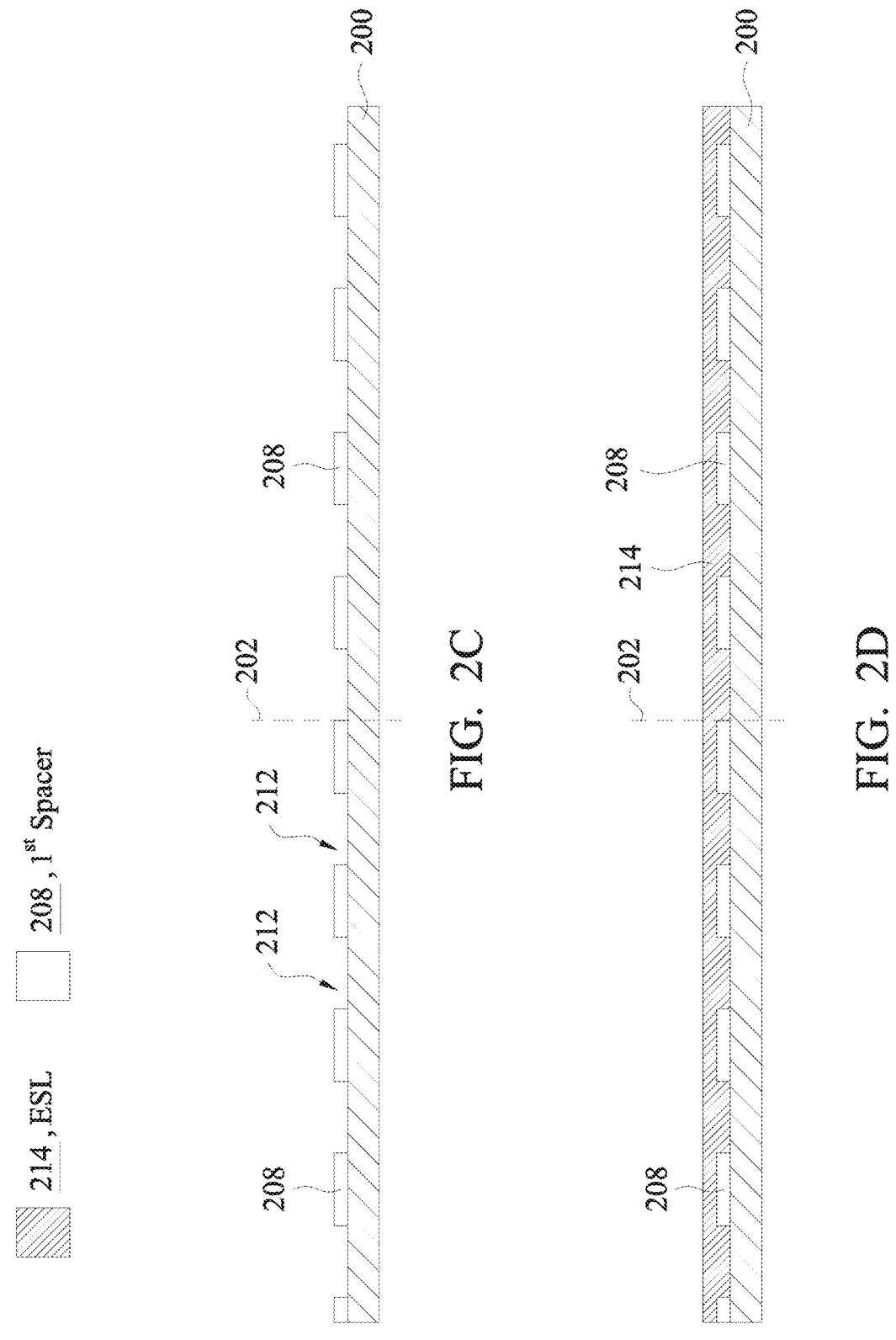
Figures 2E, 2F:
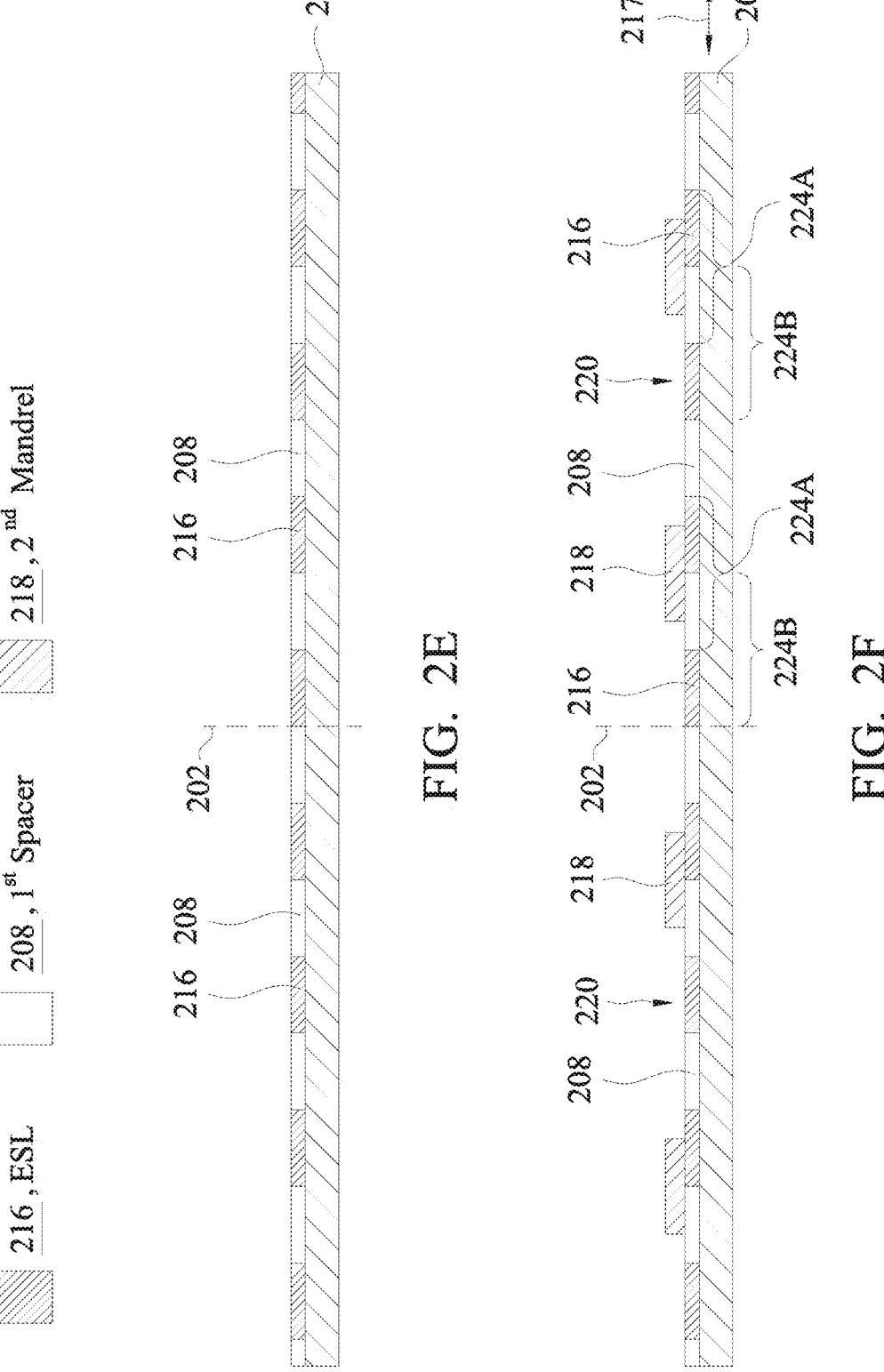
Figures 2G, 2H:
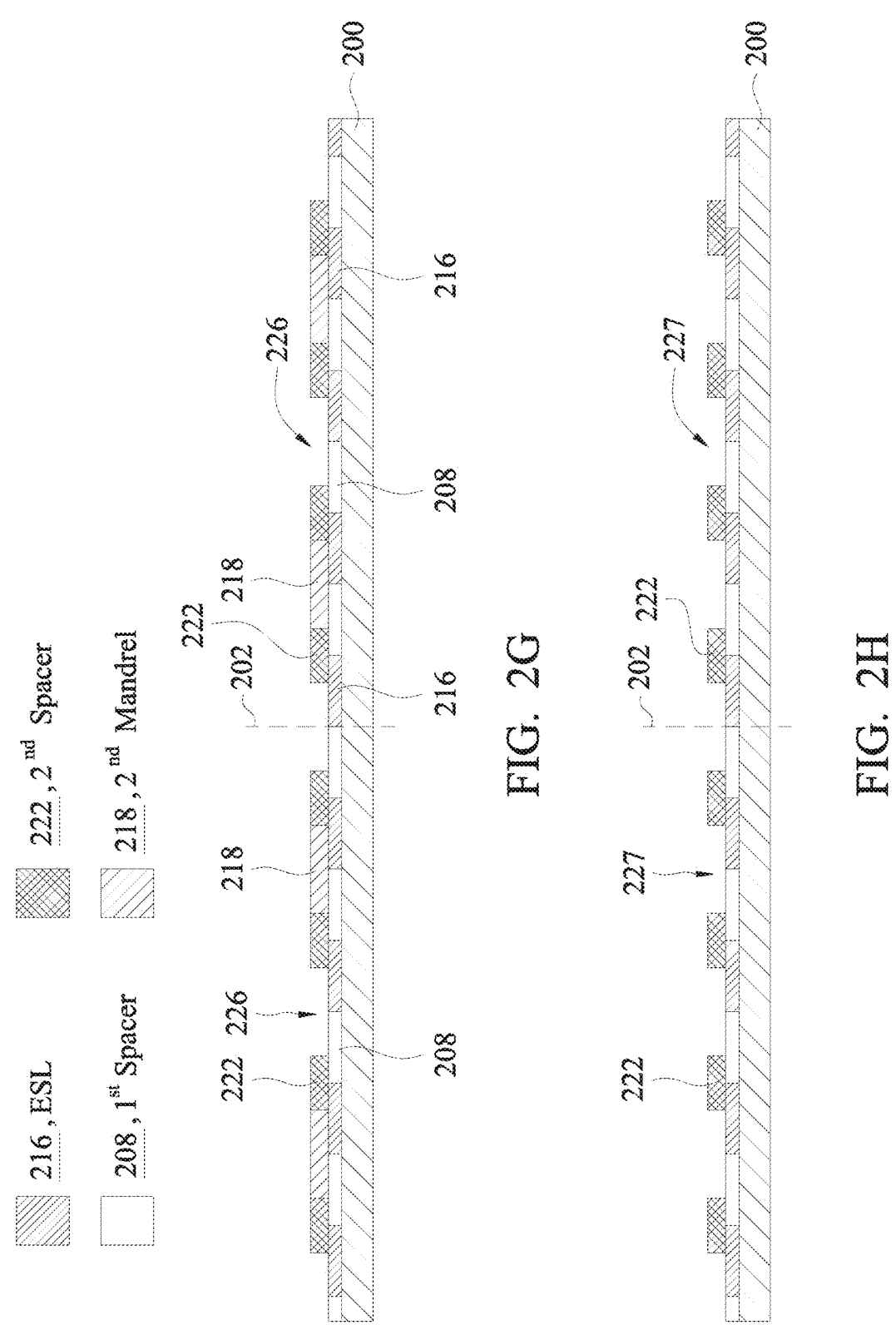
Figures 2I, 2J:
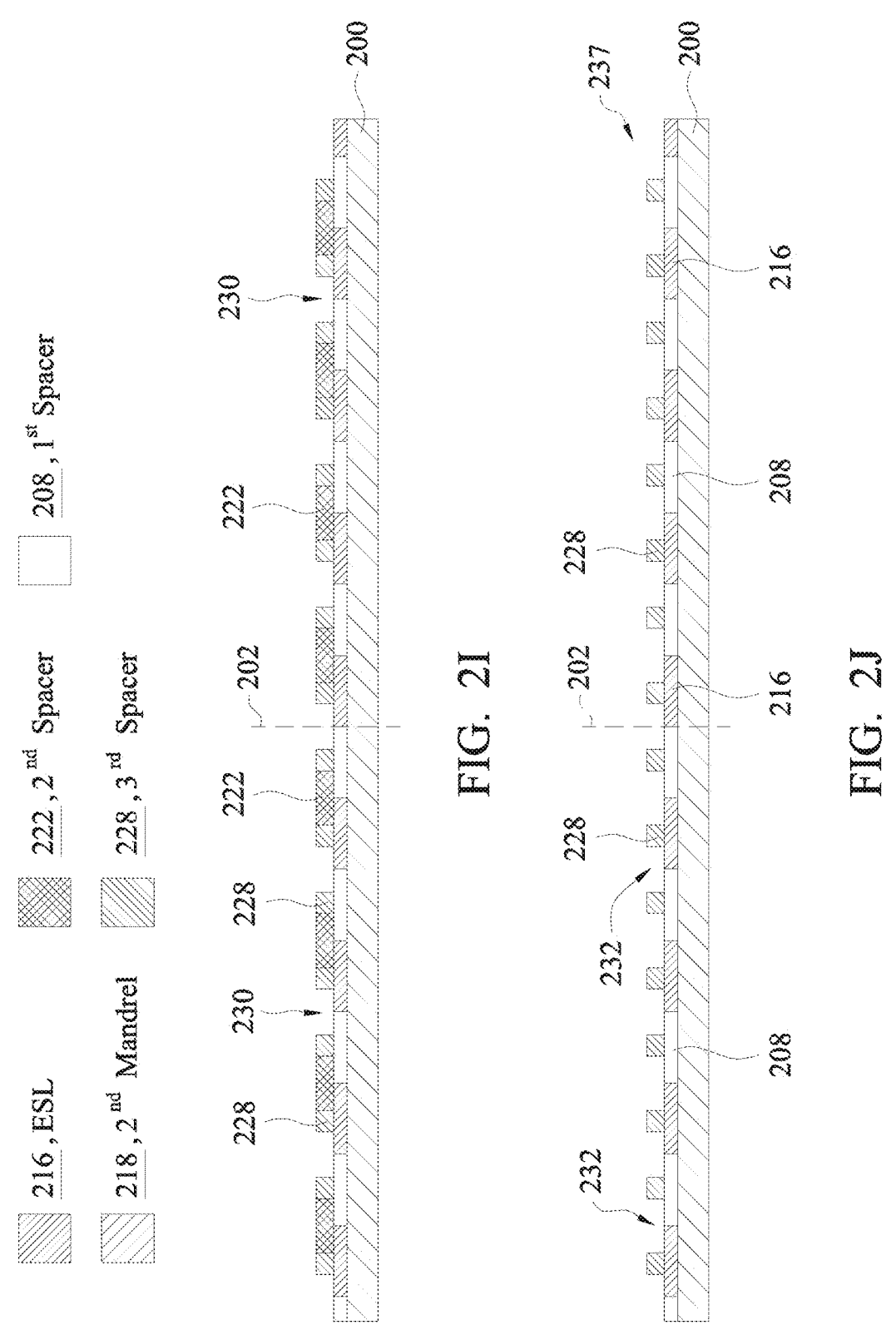
Figures 2K, 2L:
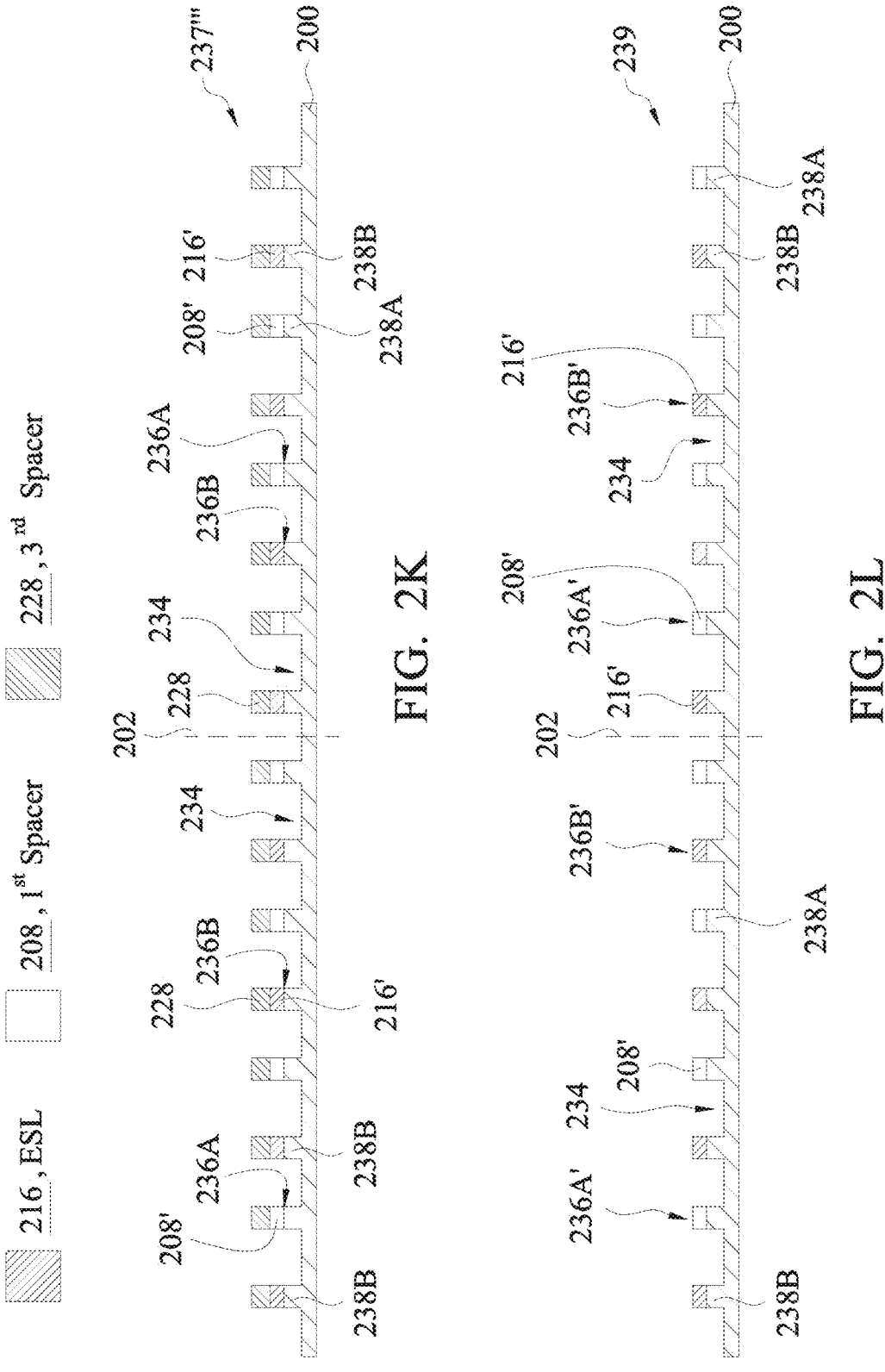
Figures 2M, 2N:
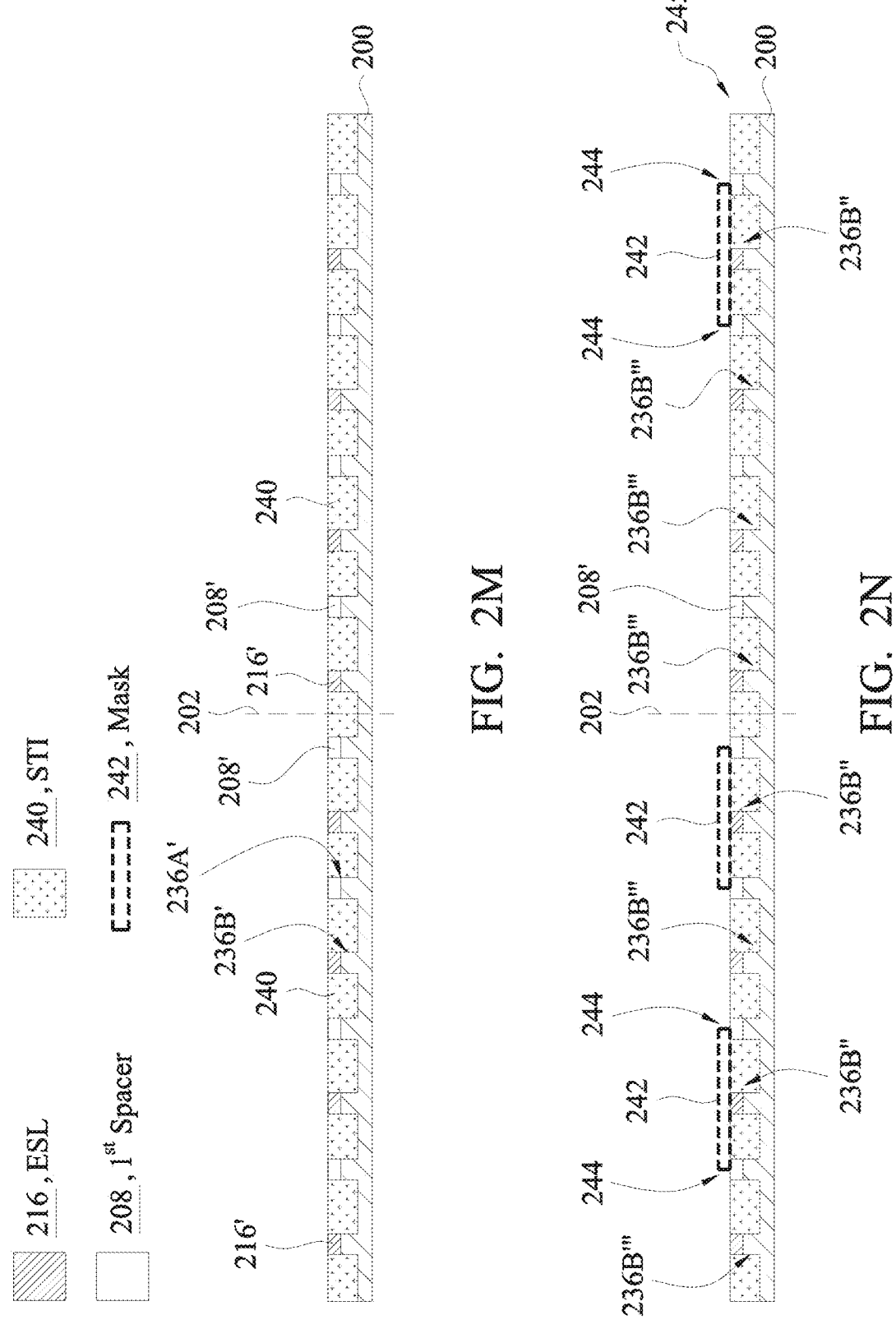

In some embodiments, block 104 corresponds to FIGS. 2A-2K, where FIG. 2K is the result of block 104. In some embodiments, block 104 corresponds to FIGS. 2A-2L, where FIG. 2L is the result of block 104. In some embodiments, block 104 corresponds to FIGS. 2A-2M, where FIG. 2M is the result of block 104.

Figures 3D, 3E:
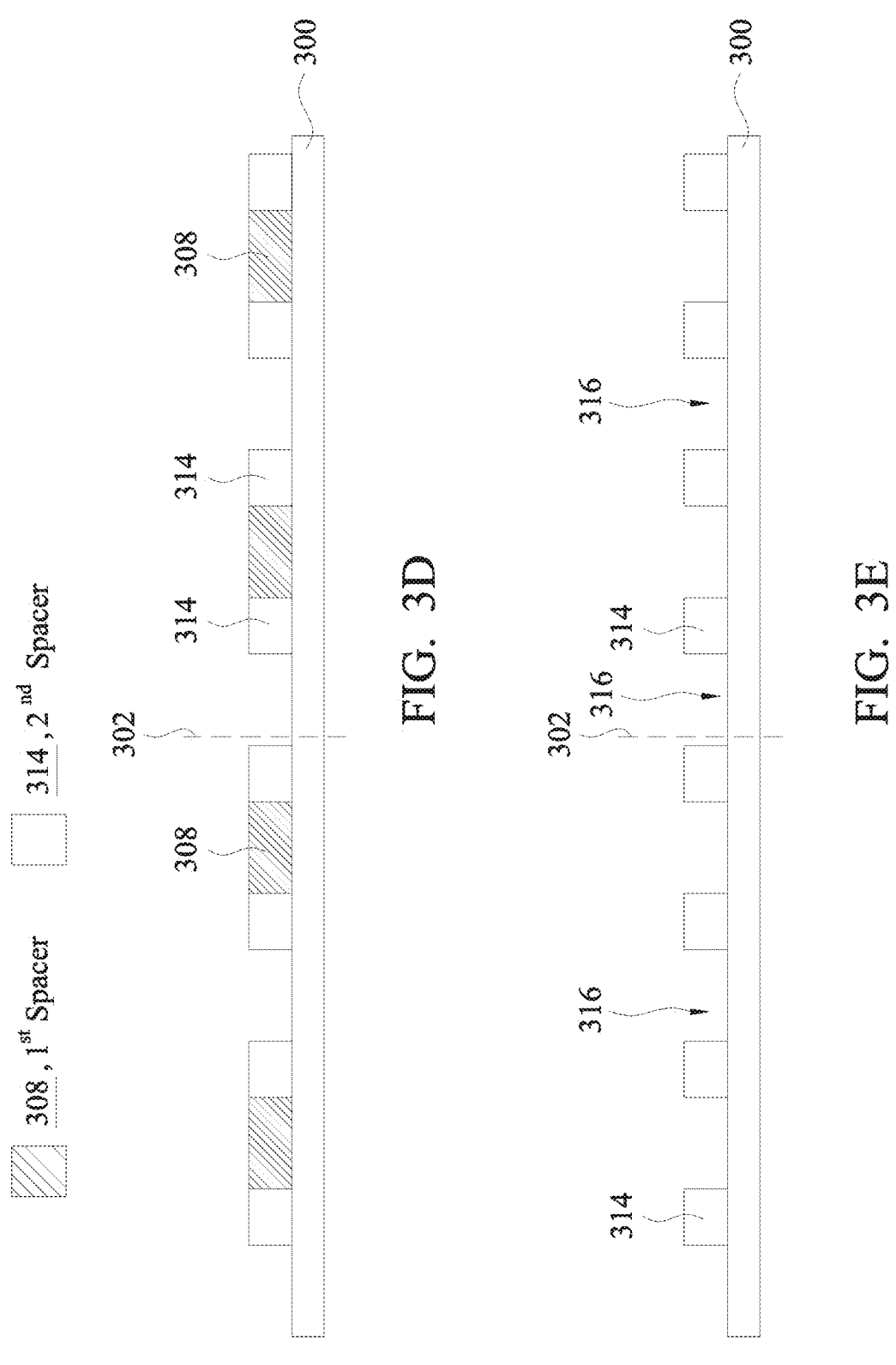
FIGS. 3A-3V are cross-sections of other various stages in the manufacture of fins for a semiconductor device which includes Fin-FETs in accordance with at least one embodiment of the present disclosure.
Figures 3F, 3G:
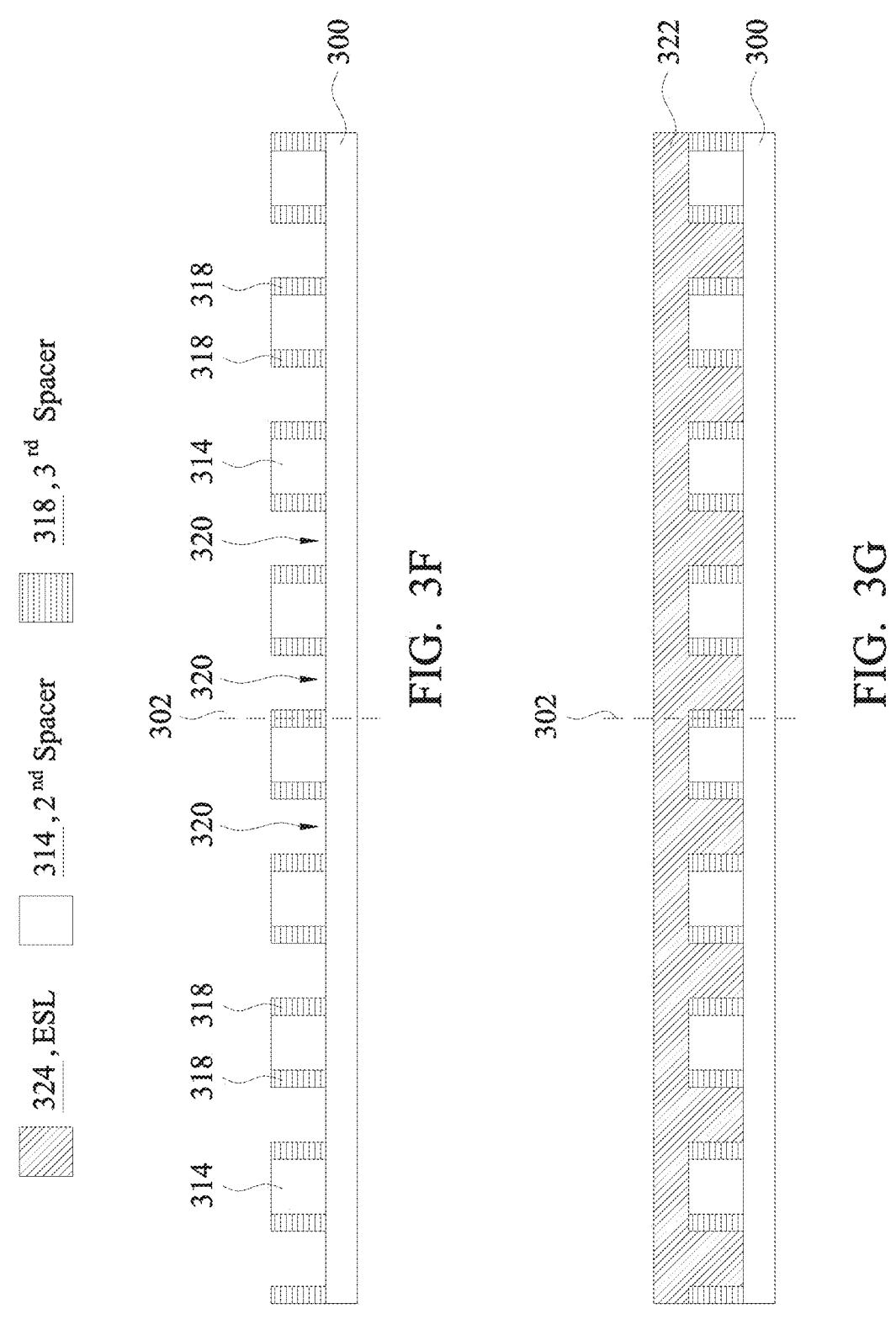
Figures 3H, 3I:
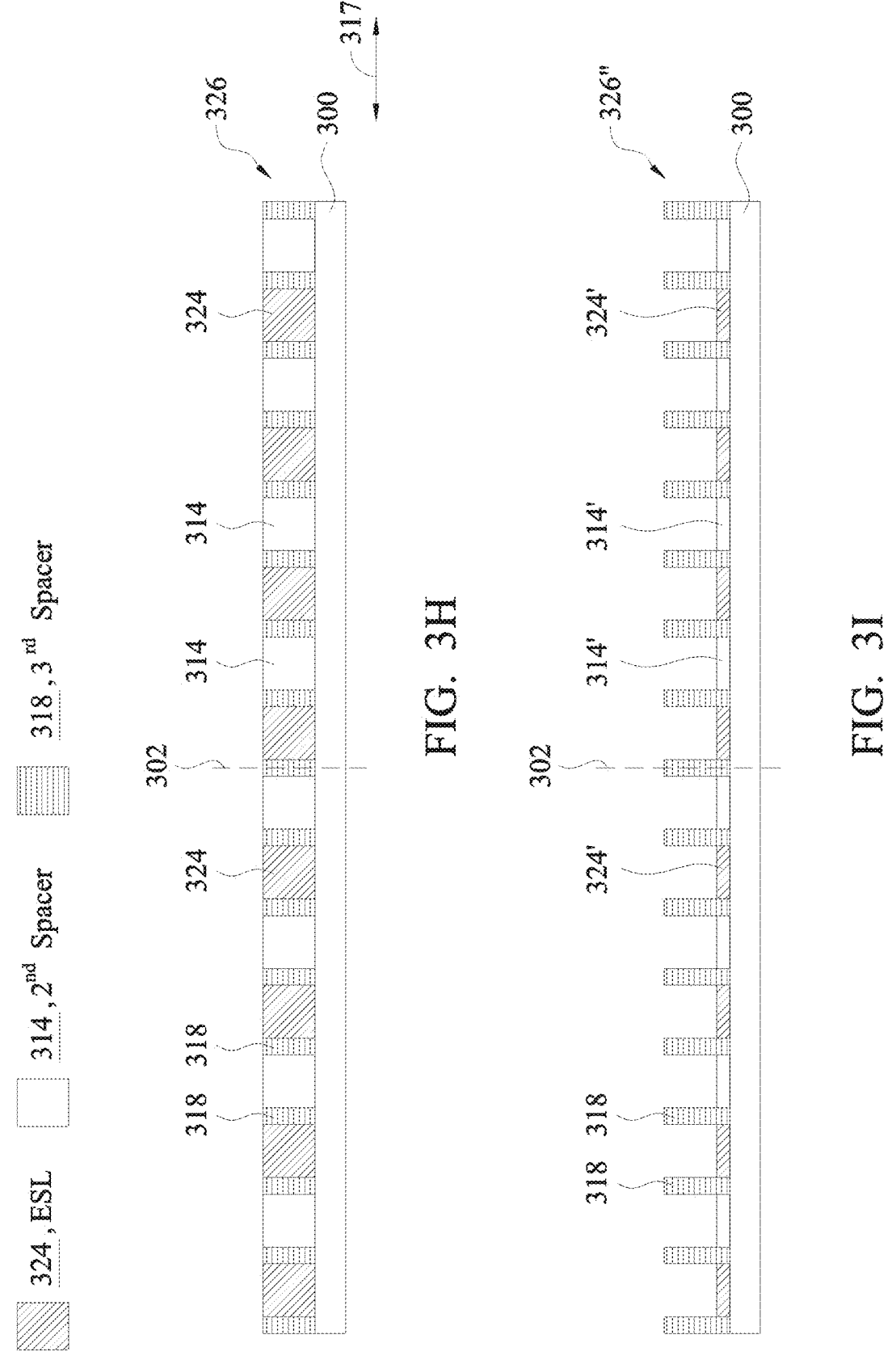
Figures 3J, 3K:
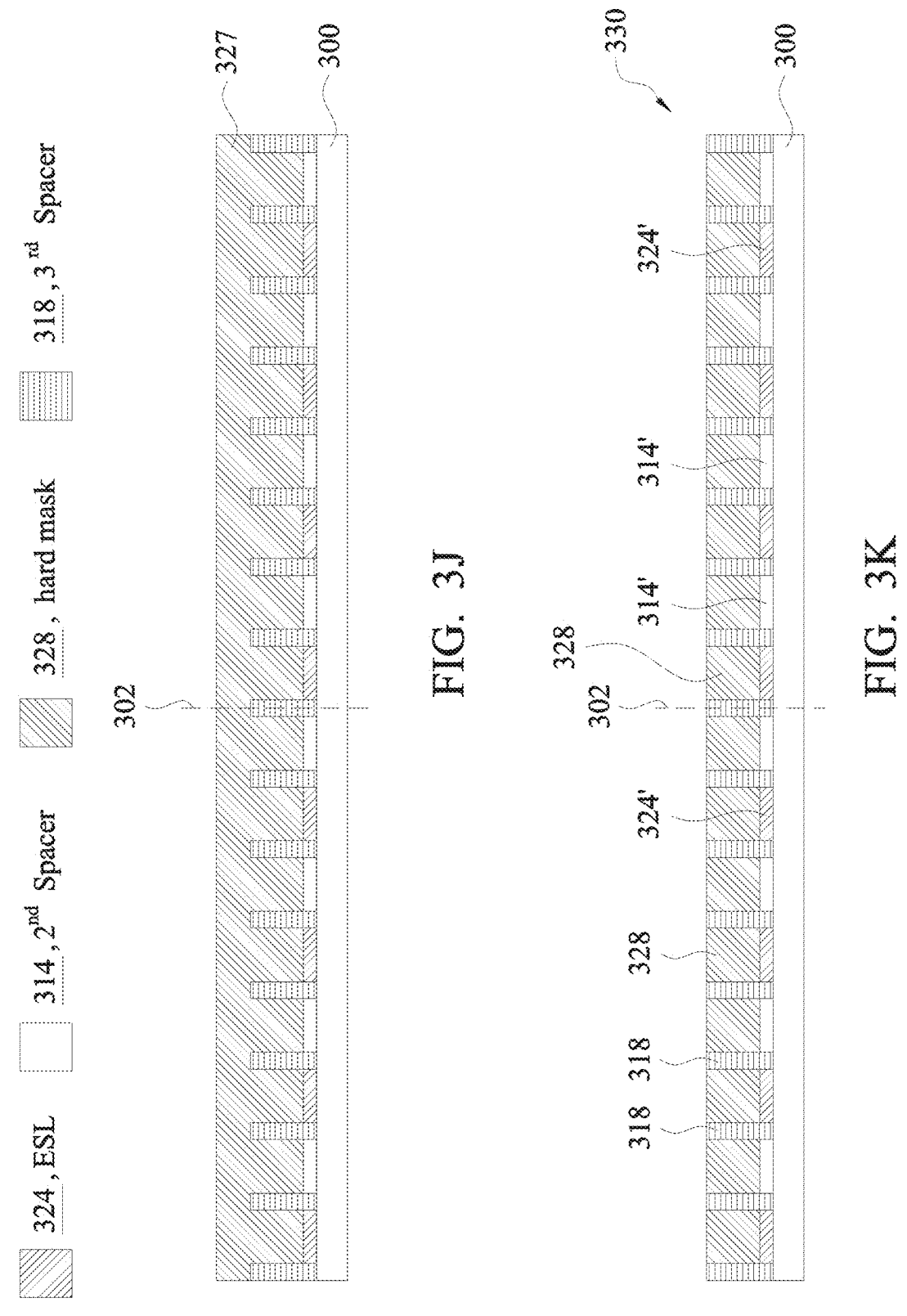
Figures 3L, 3M:
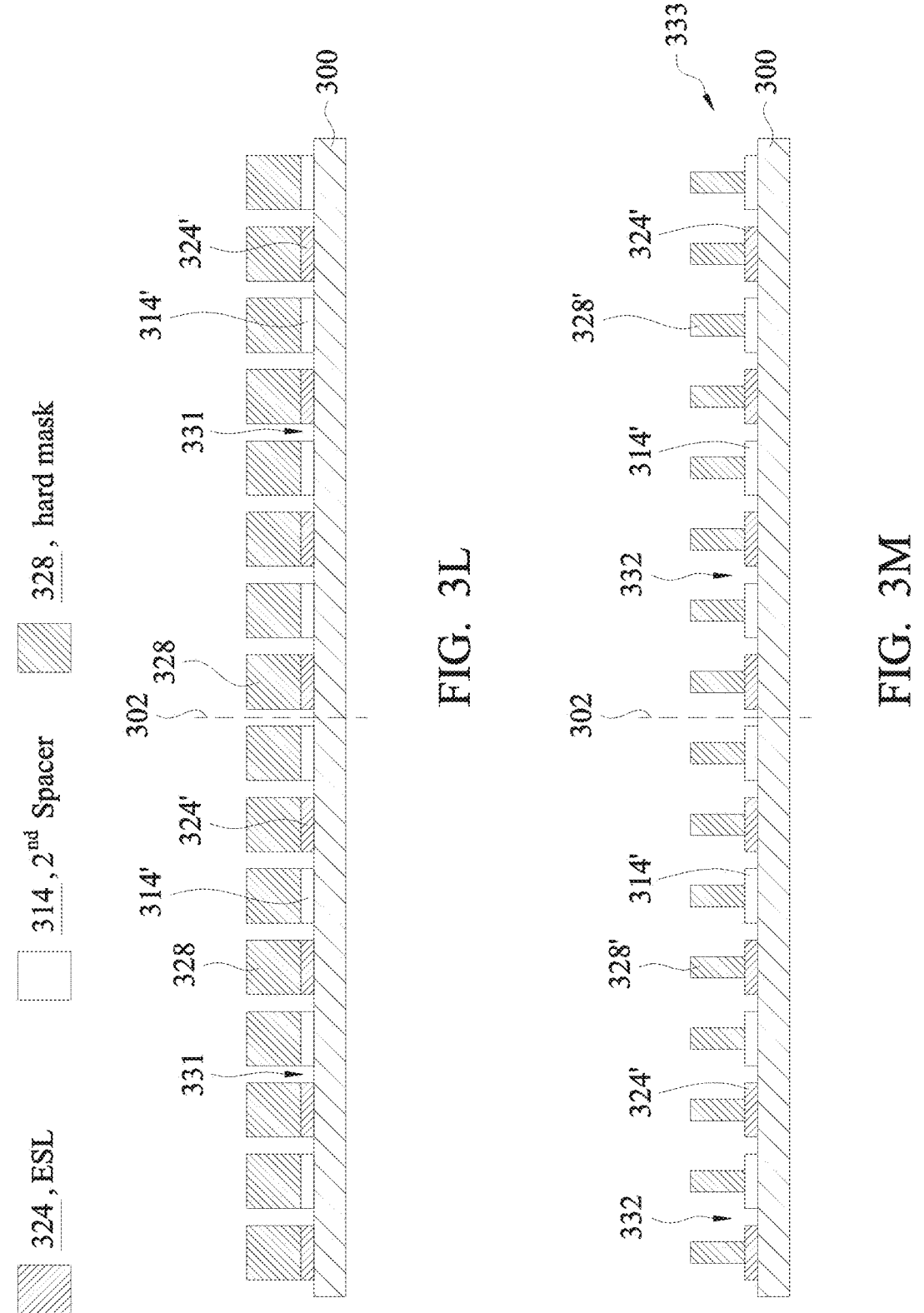
Figures 3N, 3O:
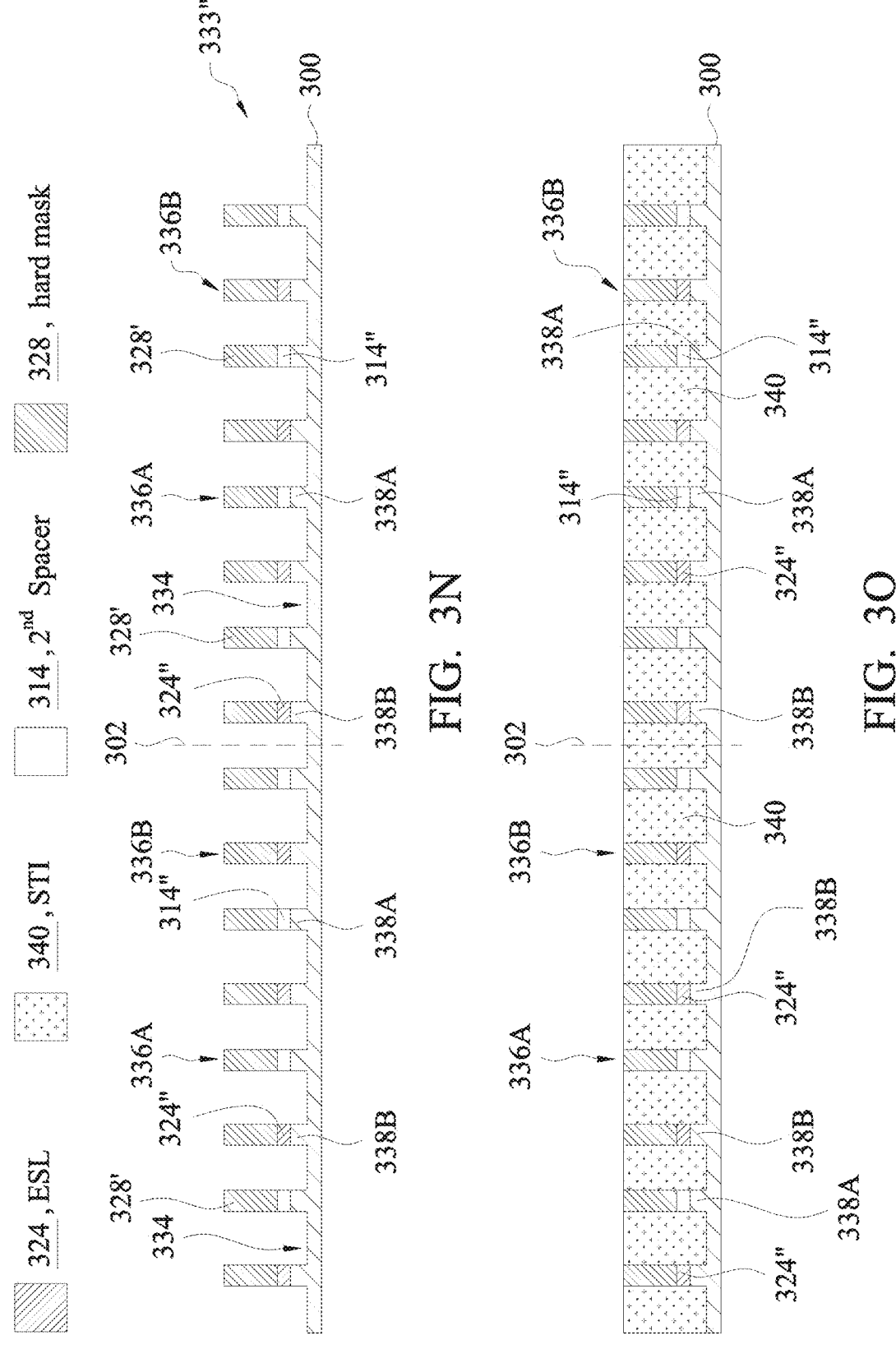
Figures 3P, 3Q:
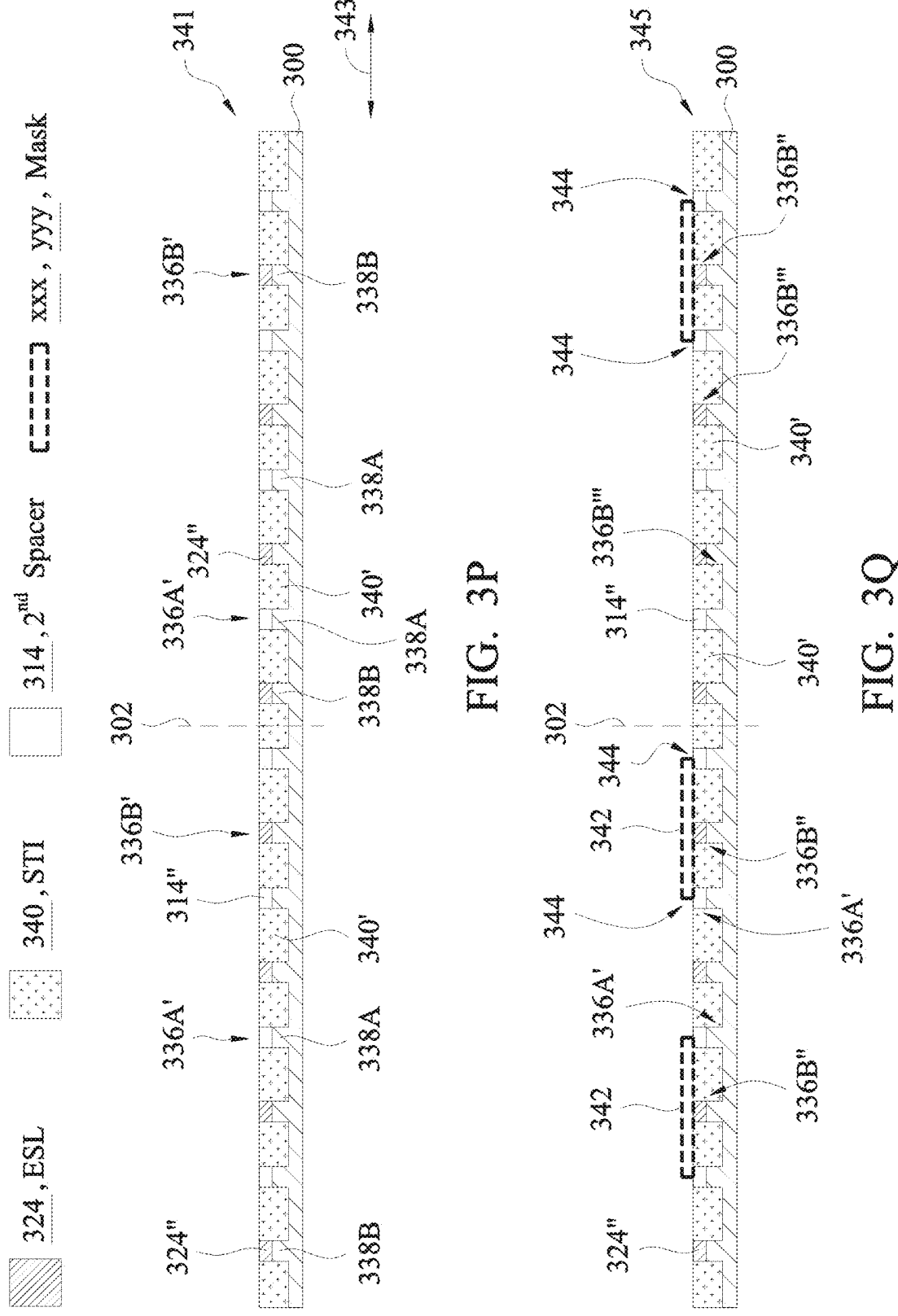

In some embodiments, block 104 corresponds to FIGS. 3A-3N, where FIG. 3N is the result of block 104. In some embodiments, block 104 corresponds to FIGS. 3A-3O, where FIG. 3O is the result of block 104. In some embodiments, block 104 corresponds to FIGS. 3A-3P, FIG. 3P is the result of block 104.

At block 106, selected members of the first set and selected members of the second set are eliminated from the structure. From block 106, flow proceeds to a block 108.

Figures 2O, 2P:
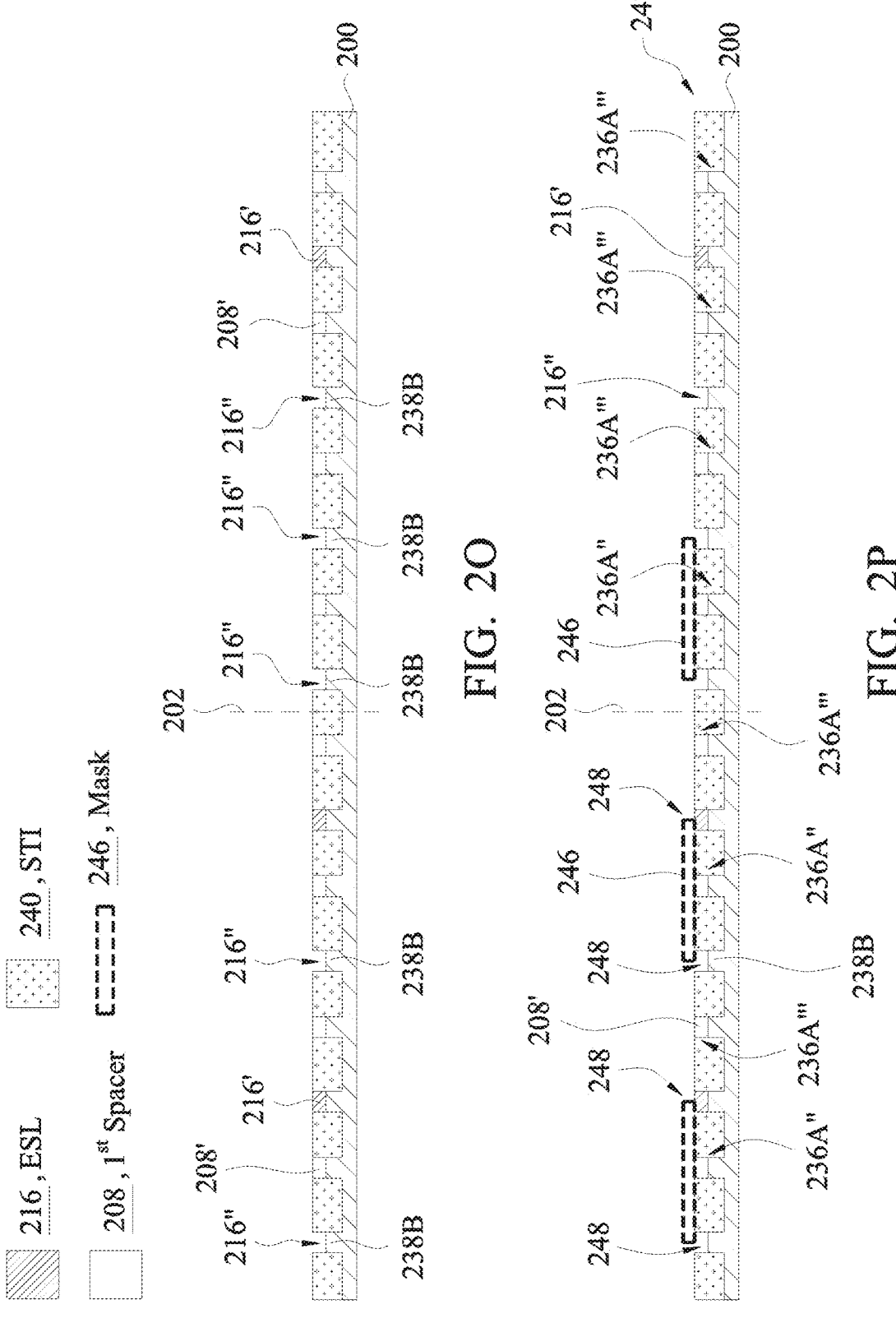
Figures 2Q, 2R:
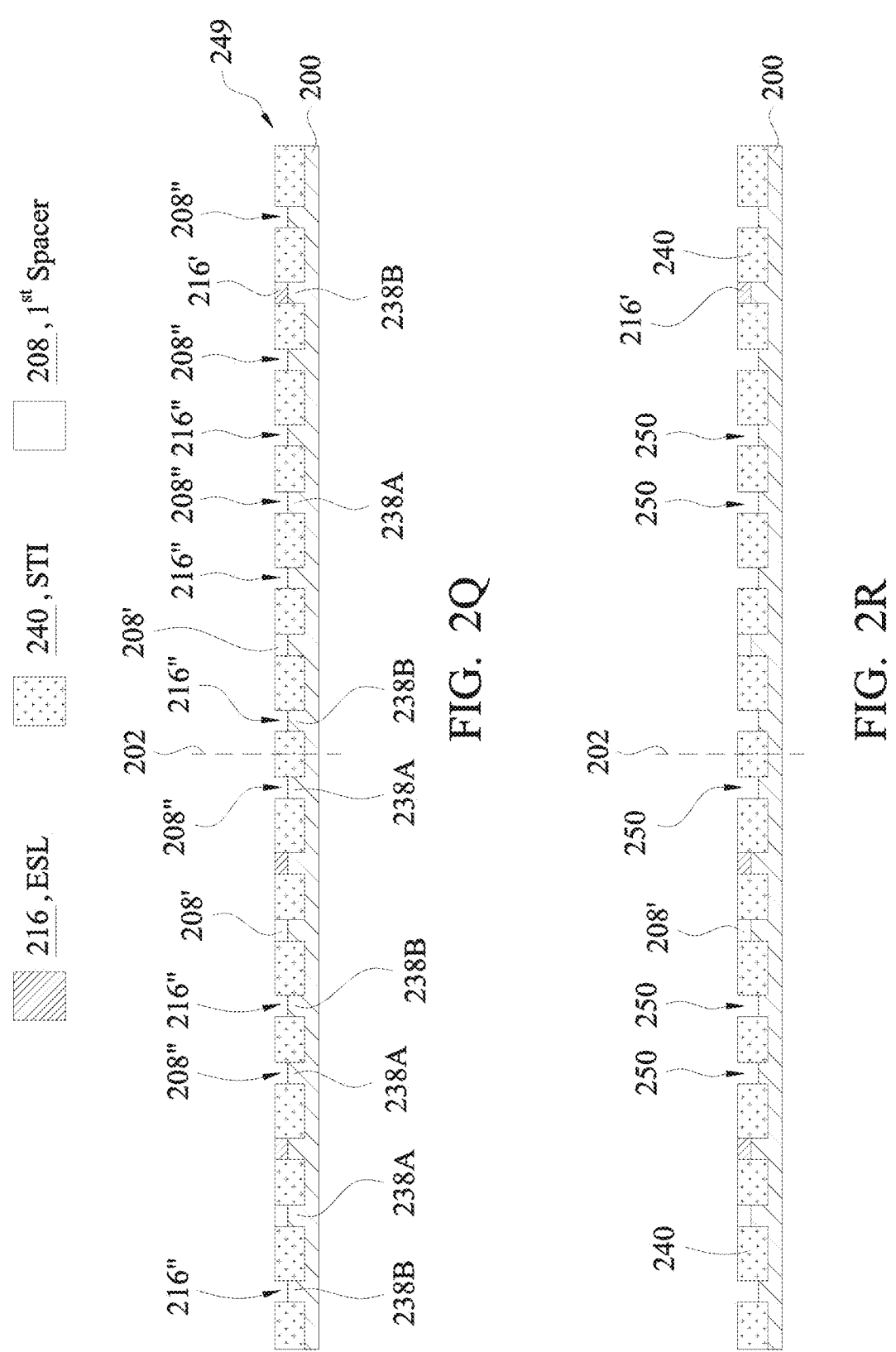
Figure 2S:
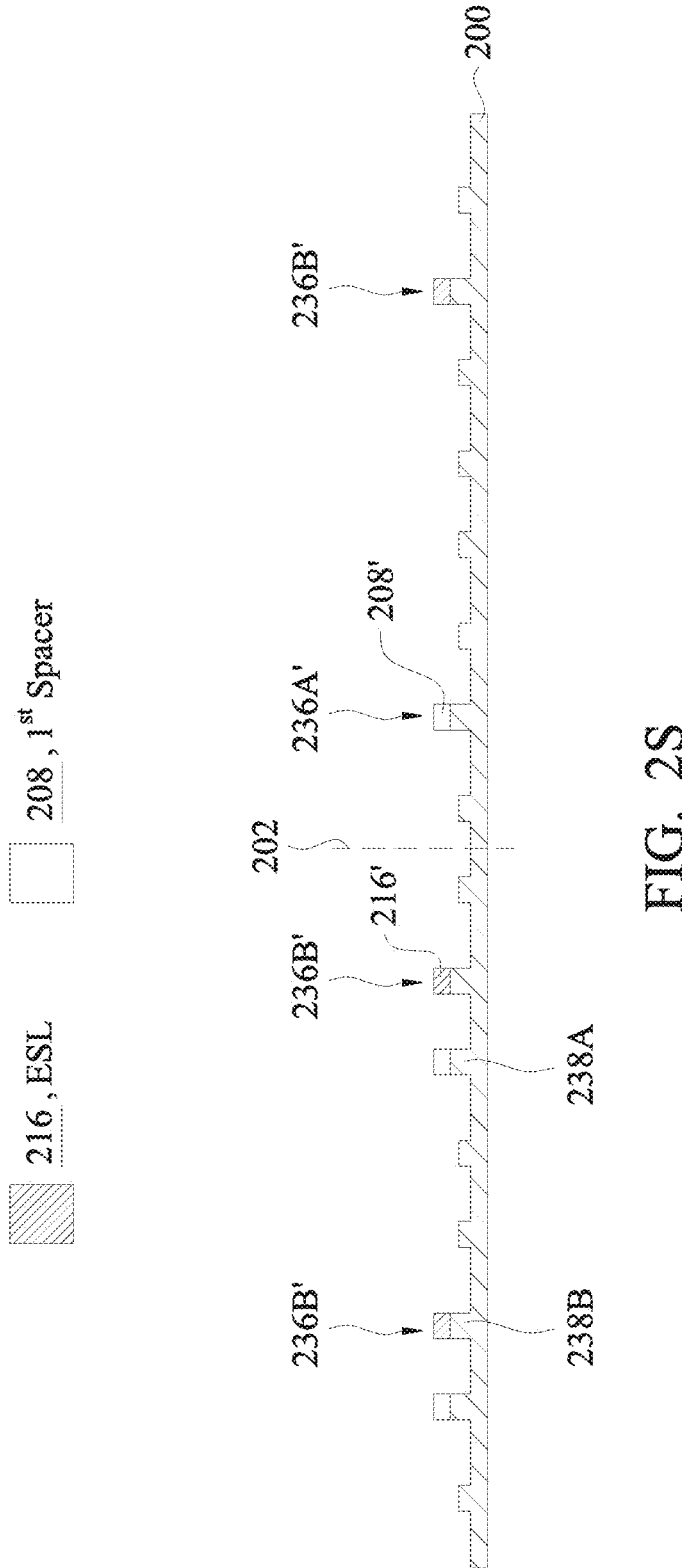

In some embodiments, block 106 corresponds to FIGS. 2L-2S, where FIG. 2S is the result of block 106. In some embodiments, block 106 corresponds to FIGS. 2M-2S, where FIG. 2S is the result of block 106. In some embodiments, block 106 corresponds to FIGS. 2N-2S, where FIG. 2S is the result of block 106.

Figures 3R, 3S:
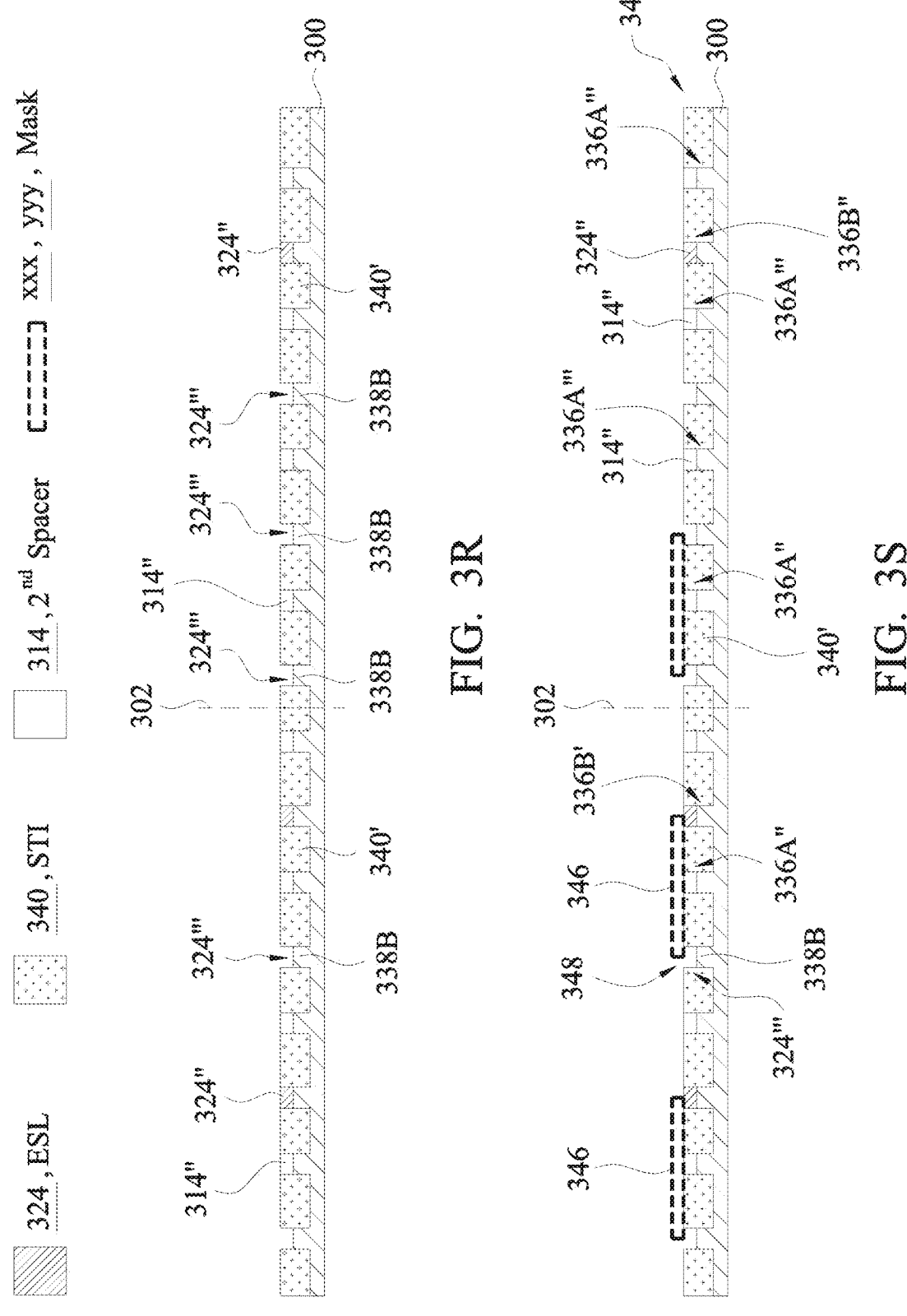
Figures 3T, 3U:
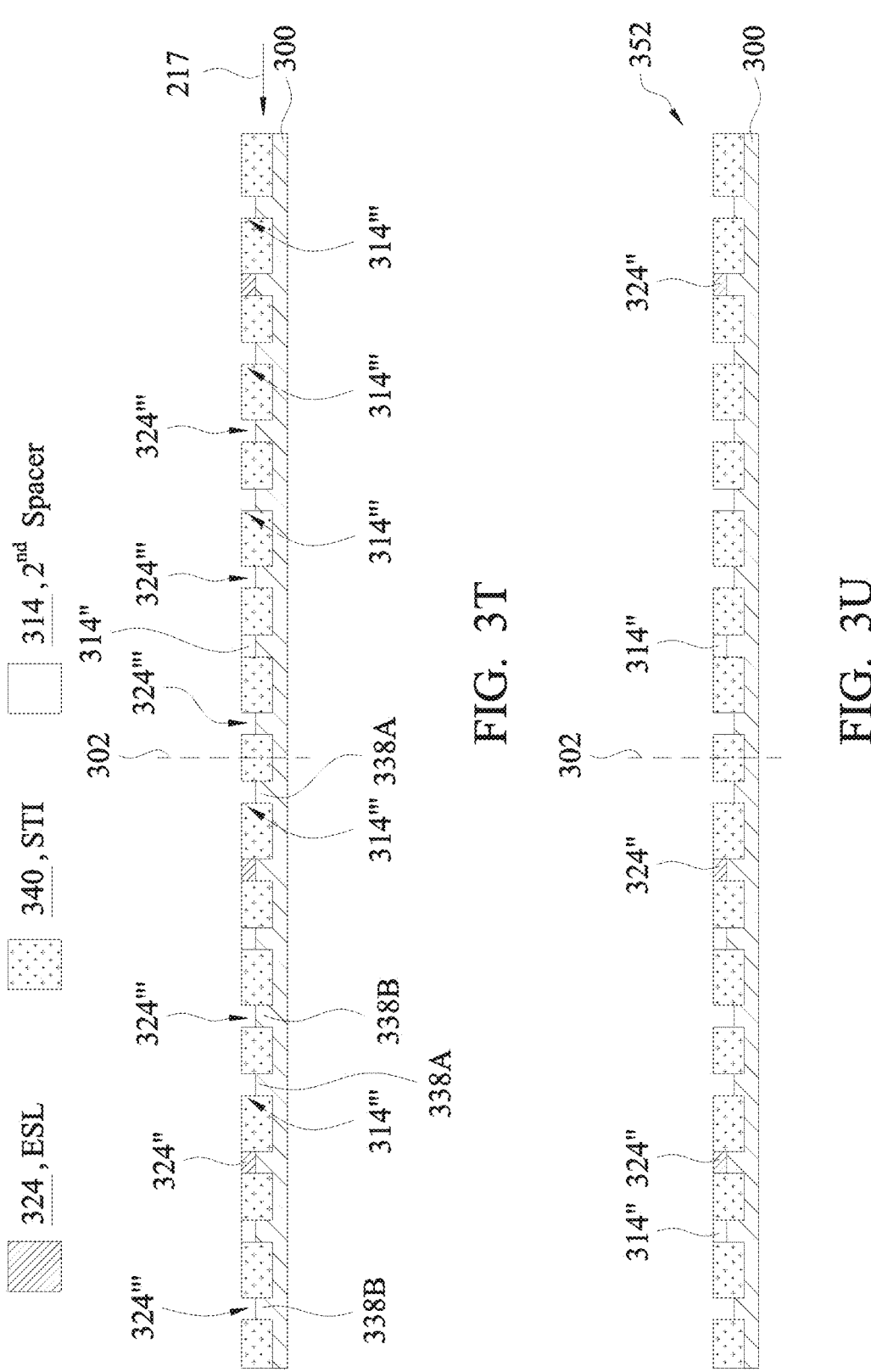
Figure 3V:
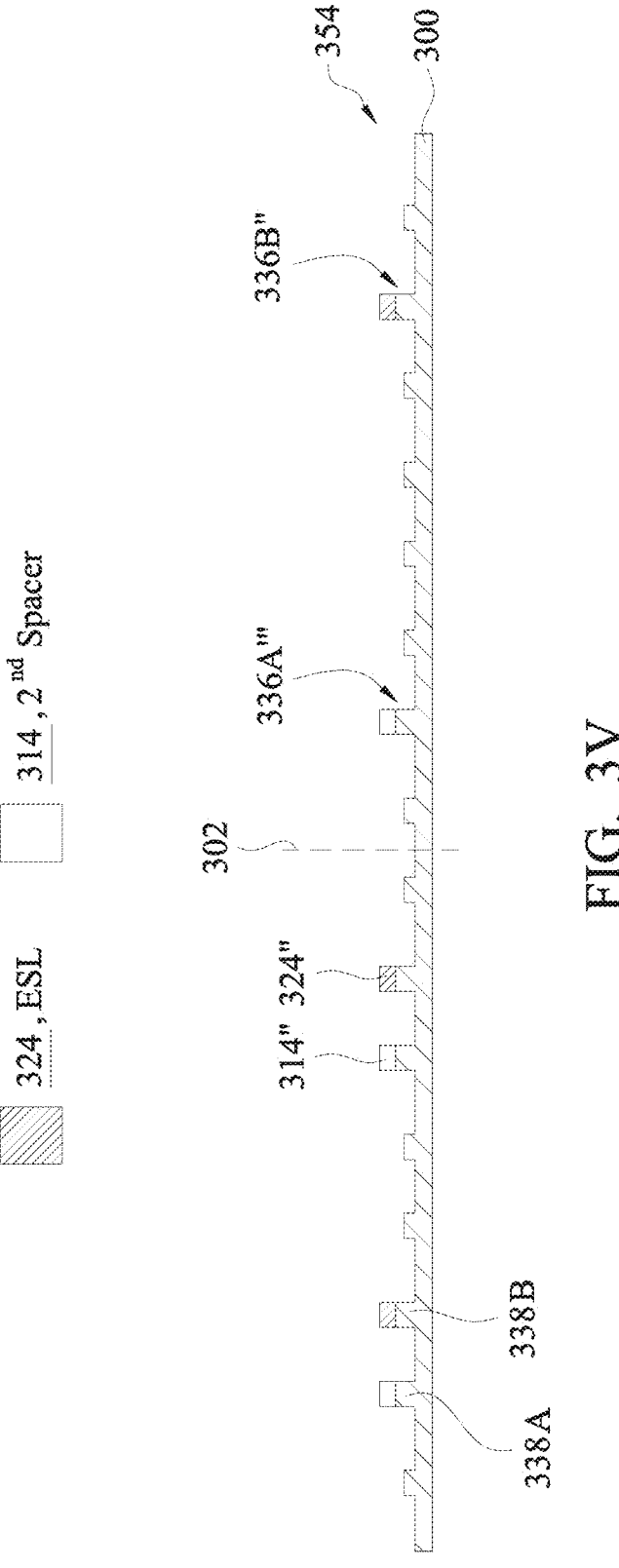

In some embodiments, block 106 corresponds to FIGS. 3O-3V, where FIG. 3V is the result of block 106. In some embodiments, block 106 corresponds to FIGS. 3P-3V, where FIG. 3V is the result of block 106. In some embodiments, block 106 corresponds to FIGS. 3Q-3V, where FIG. 3V is the result of block 106.

In some embodiments, block 106 is implemented as blocks 110, 112 and 114. At block 110, the second caps of selected members of the second set are removed to form second uncapped fins. As a result, the second set is reduced to include only unselected members. From block 110, flow proceeds to a block 112.

In some embodiments, block 110 corresponds to FIGS. 2L-2O, where FIG. 2O is the result of block 110. In some embodiments, block 110 corresponds to FIGS. 2M-2O, where FIG. 2O is the result of block 110. In some embodiments, block 110 corresponds to FIGS. 2N-2O, where FIG. 2O is the result of block 110.

In some embodiments, block 110 corresponds to FIGS. 3O-3R, where FIG. 3R is the result of block 110. In some embodiments, block 110 corresponds to FIGS. 3P-3R, where FIG. 3R is the result of block 110. In some embodiments, block 110 corresponds to FIGS. 3Q-3R, where FIG. 3R is the result of block 110.

At block 112, the first caps of selected members of the first set are removed to form first uncapped fins. As a result, the first set is reduced to include only unselected members. From block 112, flow proceeds to a block 114.

In some embodiments, block 112 corresponds to FIGS. 2P-2Q, where FIG. 2Q is the result of block 112. In some embodiments, block 112 corresponds to FIGS. 3S-3T, where FIG. 3T is the result of block 112.

At block 114, the first and second uncapped fins, which correspond to the selected members of the first and second sets, are reduced in height. In some embodiments, as a result, residual fins of negligible height remain. In some embodiments, no residual of the selected members of the first and second sets remains. From block 114, flow proceeds to block 108.

In some embodiments, block 114 corresponds to FIGS. 2R-2S, where FIG. 2S is the result of block 114. In some embodiments, block 114 corresponds to FIGS. 3U-3V, where FIG. 3V is the result of block 114.

At block 108, the remainder of the semiconductor device (which includes Fin-FETs) is formed. In some embodiments, block 108 includes at least implanting dopants to form wells and channels, forming gate dielectrics, forming lightly doped source/drain region, and forming gate stacks.

FIGS. 2A-2S are cross-sections of various stages in the manufacture of fins for a semiconductor device which includes Fin-FETs in accordance with at least one embodiment of the present disclosure.

In some embodiments, FIGS. 2A-2K correspond to block 104 of FIG. 1, where FIG. 2K is the result of block 104, and FIGS. 2L-2S correspond to block 106 of FIG. 1, where FIG. 2S is the result of block 106. In some embodiments, FIGS. 2A-2L correspond to block 104 of FIG. 1, where FIG. 2L is the result of block 104, and FIGS. 2M-2S correspond to block 106 of FIG. 1, where FIG. 2S is the result of block 106. In some embodiments, FIGS. 2A-2M correspond to block 104 of FIG. 1, where FIG. 2M is the result of block 104, and FIGS. 2N-2S correspond to block 106 of FIG. 1, where FIG. 2S is the result of block 106.

In FIG. 2A, first mandrel features 204 are built on a substrate 200, which leaves first regions 206 of substrate 200 exposed.

In some embodiments, substrate 200 is silicon, e.g., a silicon wafer. In some embodiments, substrate 200 is amorphous silicon (a-Si). Substrate 200 may be formed by a variety of processes. In some embodiments, substrate 200 is formed over another substrate by a procedure such as deposition. In some embodiments, other materials, such as carbon, germanium, gallium, arsenic, nitrogen, indium, and/or phosphorus, are included in substrate 200. In some embodiments, substrate 200 is a bulk substrate or a semiconductor-on-insulator (SOI) substrate.

In some embodiments, the fins that result from the various stages of manufacture of FIGS. 2A-2S are incorporated in a semiconductor device which includes Fin-FETs, with at least some of the fins being included in SRAM memory cells. In such embodiments, dashed line 202 represents a border between adjacent SRAM memory cells.

In some embodiments, first mandrel features 204 are built in a layer of negative or positive photoresistive material using a photolithography process. In some embodiments, first mandrel features 204 are built by spin-coating a negative photoresist layer over substrate 200, soft baking the photoresist layer, exposing the photoresist layer to light (e.g., a deep ultraviolet (DUV) light) using a mask. Then the exposed photoresist layer is subjected to post-exposure baking (PEB), developing, and hard baking thereby removing unexposed portions of the photoresist layer and leaving exposed portions of the photoresist layer on substrate 200 as first mandrel features 204. In some embodiments, first mandrel features 204 are built by unexposed portions of a positive resist material layer in a similar photolithography process. In some embodiments, first mandrel features 204 are evenly distributed in a reference direction 217 parallel to a plane of substrate 200. The patterned photoresist layer is removed thereafter using a suitable process, such as wet stripping or plasma ashing. In some embodiments, the etching process includes applying a dry (or plasma) etch to remove the one or more dielectric layers within the openings of the patterned photoresist layer.

In FIG. 2B, in some areas of first regions 206, first spacers 208 are built on substrate 200.

First spacers 208 abut sidewalls of first mandrel features 204, which leave second regions 210 of substrate 200 exposed. First spacers 208 include one or more materials which are different from the material from which first mandrel features 204 are built. First spacers 208 have an etch sensitivity, ES208. In some embodiments, first spacers 208 include dielectric material, such as titanium nitride, silicon nitride, titanium oxide or other suitable material. In some embodiments, other materials suitable for first spacers 208 include, but are not limited to, poly-silicon, SiO2, Si3N4, SiON, TEOS, nitrogen-containing oxide, nitride oxide, high K material (K≥5), or combinations thereof. In some embodiments, first spacers 208 are built by various processes, including a deposition process and an etching process. In some embodiments, the deposition process includes a chemical vapor deposition (CVD) process, a physical vapor deposition (PVD) process or another suitable process. In some embodiments, first spacers 208 are built by CVD using chemicals including Hexachlorodisilane (HCD or Si2Cl6), Dichlorosilane (DCS or SiH2Cl2), Bis(TertiaryButylAmino) Silane (BTBAS or C8H22N2Si) and/or Disilane (DS or Si2H6). In some embodiments, first spacers 208 are silicon oxide formed by thermal oxidation. In some embodiments, first spacers 208 are SiN formed by chemical vapor deposition (CVD).

In FIG. 2C, first mandrel features 204 are removed, which leaves third regions 212 of substrate 200 exposed.

Third regions 212 are larger than second regions 210. In some embodiments, first mandrel features 204 are removed by an etching process tuned to remove the material from which first mandrel features 204 are built but not first spacers 208. In some embodiments, the etching process is a wet etching, a dry etching, or a combination thereof. First spacers 208 are used as hard masks during subsequent etching processes.

In FIG. 2D, a layer 214 of etch stop material is deposited on first spacers 208 and third regions 212 of substrate 200.

In some embodiments, layer 214 is formed of silicon nitride, e.g., using low-pressure chemical vapor deposition (LPCVD). In some embodiments, layer 214 is formed by thermal nitridation of silicon, plasma enhanced chemical vapor deposition (PECVD), plasma anodic nitridation or another suitable process. In some embodiments, layer 214 includes multiple layers of material to gain process flexibility. In some embodiments, layer 214 includes a first oxide layer deposited on first spacers 208 and third regions 212 of substrate 200, a silicon nitride layer deposited on the first oxide layer, and a second silicon oxide layer deposited on the silicon nitride layer. In some embodiments, the one or more layers comprising layer 214 are formed by thermal oxidation, a chemical vapor deposition (CVD) process, plasma enhanced CVD (PECVD) and/or atomic layer deposition (ALD).

In FIG. 2E, a portion of layer 214 is removed, which leaves etch stop layer (ESL) portions 216 on substrate 200.

ESL portions 216 abut sidewalls of first spacers 208. ESL portions 216 have an etch sensitivity, ES216, etch sensitivity ES216 being different than etch sensitivity ES208. In some embodiments, ES216≥ES208. In some embodiments, ES208≥ES216. In some embodiments, the portion of layer 214 is removed using chemical mechanical polishing (CMP). In some embodiments, the CMP produces an approximately planar surface. In some embodiments, relative to reference direction 217: widths of first spacers 208 and ESL portions 216 are approximately (if not nearly exactly) the same. ESL portions 216 are used as hard masks during subsequent etching processes.

In FIG. 2F, second mandrel features 218 are built on areas of the first spacers and ESL portions, thereby leaving fourth regions 220 of the first spacers and ESL portions exposed.

In some embodiments, the first spacers and ESL portions are interleaved into a sequence of pairs, and second mandrel features 218 are centered over alternating ones 224A of the pairs (mandrel-centering pairs 224A). In some embodiments, second mandrel features 218 are built in a manner similar to how first mandrel features 204 are built.

In FIG. 2G, second spacers 222 are built in some areas of fourth regions 220 on first spacers 208 and ESL portions 216.

Second spacers 222 abut sidewalls of second mandrel features 218, which leaves fifth regions 226 of the first spacers and ESL portions exposed. In some embodiments, second spacers 222 are built in a manner similar to how first spacers 208 are built. In some embodiments, relative to reference direction 217: mandrel-centering pairs 224A overlap other ones 224B of the pairs (spacer-centering pairs 224B) such that first spacer 208 of a given mandrel-centering pair 224A is also a member of a first instance of spacer-centering pairs 224B and ESL portion 216 of the given mandrel-centering pair 224A is also a member of a second instance of spacer-centering pairs 224B. As such, the widths of second spacers 222 are set such that second spacers 222 are centered over corresponding spacer-centering pairs 224B.

In FIG. 2H, second mandrel features 218 are removed, which leaves sixth regions 227 of first spacers 208 and ESL portions 216 exposed.

In some embodiments, second mandrel features 218 are removed by an etching process tuned to remove the material from which second mandrel features 218 are built but not second spacers 222. In some embodiments, the etching process is a wet etching, a dry etching, or a combination thereof.

In FIG. 2I, third spacers 228 are built on areas of sixth regions 227 of first spacers 208 and ESL portions 216, which leaves seventh regions 230 of first spacers 208 and ESL portions 216 exposed.

Third spacers 228 abut sidewalls of second spacers 222. In some embodiments, third spacers 228 and second spacers 222 are built in a manner similar to how first spacers 208 and second spacers 222 are built. Third spacers 228 have an etch sensitivity, ES228, with ES228 being different than etch sensitivity ES208 and etch sensitivity ES216. In some embodiments, ES228≥1.5*ES208 and ES228≥1.5*ES216. In some embodiments, ES208≥1.5*ES228 and ES216≥1.5*ES228.

In FIG. 2J, second spacers 222 are removed, which leaves seventh regions 232 of first spacers 208 and ESL portions 216 exposed, which results in an intermediate structure 237.

In some embodiments, second spacers 222 are removed by etching. In some embodiments, the etching process is a wet etching, a dry etching, or a combination thereof.

In FIG. 2K, exposed seventh regions 232 of first spacers 208 and ESL portions 216 and a layer of substrate 200 lying thereunder are removed, which leaves eighth regions 234 of substrate 200 exposed, and thereby results in an intermediate structure 237'''.

Intermediate structure 237''' includes inchoate versions 236A and 236B of capped semiconductor fins 236A' and 236B'. An inchoate version refers to a version which is not yet completed or fully developed. Here, because third spacers 228 remain, versions 236A and 236B are referred to as inchoate. In some embodiments, exposed seventh regions 232 of first spacers 208 and ESL portions 216 and a layer of substrate 200 lying thereunder are removed in a multi-step etching process. In some embodiments, the multi-step etching process includes at least three steps. In the first step, intermediate structure 237 is etched with a first etchant appropriate to first etch sensitivity ES208 of first spacers 208, which results in an intermediate structure 237' (not shown). In the second step, intermediate structure 237' is etched with a second etchant appropriate to second etch sensitivity ES216 of ESL portions 216, which results in an intermediate structure 237'' (not shown). In the third step, intermediate structure 237'' is etched with a fourth etchant appropriate to an etch sensitivity ES200 of substrate 200, which results in intermediate structure 237'''. In some embodiments, the fourth etchant includes a selective wet etch or a selective dry etch. In some embodiments, the third step is wet etching that uses an etching solution including tetramethylammonium hydroxide (TMAH), HF/HNO3/ CH3COOH solution or another suitable solution. In some embodiments, the third step is a dry etching process, e.g., a biased plasma etching process that uses a chlorine-based chemistry. In some embodiments, other dry etchant gasses include CF4, NF3, SF6, and He. In some embodiments, the order of the first and second etching steps is reversed. In some embodiments, each of the first and second etching steps etch substrate 200, thus eliminating a need for the third etching step.

In FIG. 2L, third spacers 228 are removed, thereby forming a plurality of capped semiconductor fins 236A' and 236B', which results in an intermediate structure 239.

Intermediate structure 239 is an example of a structure that includes a semiconductor substrate (namely, substrate 200) and a plurality of capped semiconductor fins (namely, capped semiconductor fins 236A' and 236B'). Capped fins 236A' include semiconductor fins 238A capped with caps 208' which are residual portions of first spacers 208. Caps 208' have an etch sensitivity ES208', where ES208'=ES208. Capped fins 236B' include semiconductor fins 238B capped with caps 216' which are residual portions of ESL portions 216. Caps 216' have an etch sensitivity ES216', where ES216'=ES216. In some embodiments, third spacers 228 are removed by etching. In some embodiments, third spacers 228 are etched with a third etchant appropriate to third etch sensitivity ES228 of third spacers 228. In some embodiments, the etching process is a wet etching, a dry etching, or a combination thereof. In some embodiments, the four etchants (namely, the first, second, third and fourth etchants) are selected from the group consisting of HF, HNO3, H2SO4 and NH4OH, with the determination of which etchant to be used as the first, second, third and fourth etchants depending upon the material to be etched. In some embodiments, etching can be implemented using inductively coupled plasma (ICP) etching, reactive-ion etching (RIE) or another etching process, which are controlled in part by tuning the input gases, e.g., CF4, Ar, O2, Cl2, CF3I, NH3 or other suitable gases.

In FIG. 2M, shallow trench isolation (STI) regions 240 are formed in eighth regions 234 of substrate 200. STI regions 240 abut sidewalls of capped semiconductor fins 236A' and 236B'.

In some embodiments, a liner oxide is formed in eighth regions 234 of substrate 200, and then the lined versions of eighth regions 234 are filled with dielectric material. In some embodiments, the liner oxide is a thermal oxide, e.g., having a thickness between about 20 Å to about 500 Å. In some embodiments, the liner oxide is formed using in-situ steam generation (ISSG). In some embodiments, the liner oxide is formed using a deposition technique that forms conformal oxide layers, such as selective area chemical vapor deposition (SACVD). In some embodiments, the dielectric material which fills the lined versions of eighth regions 234 (hereinafter, the eighth region dielectric) is silicon oxide. In some embodiments, the eighth region dielectric is SiN or SiC. In some embodiments, the eighth region dielectric is formed using a high aspect-ratio process (HARP). In some embodiments, the HARP process gases include tetraethylorthosilicate (TEOS) and O3 (ozone).

In some embodiments, eighth regions 234 of substrate 200 are filled with an isolation dielectric layer. The isolation dielectric layer includes silicon oxide, silicon nitride, silicon oxynitride, or other suitable materials, or combinations thereof. In some embodiments, the isolation dielectric layer has a multi-layer structure. In some embodiments, the isolation dielectric layer is deposited by CVD, ALD, or other suitable techniques. In some embodiments, CMP is performed subsequently to remove excess portions of the isolation dielectric layer and thereby expose caps 208' and 216' of corresponding capped semiconductor fins 236A' and 236B'. In some embodiments, the CMP provides an approximately planar surface.

After reaching the stage of FIG. 2M, over the course of subsequent stages of FIGS. 2N-2S, selected members (e.g., 236B''' of FIG. 2N) of capped semiconductor fins 236B' and selected members (e.g., 236A''' of FIG. 2P) of capped semiconductor fins 236A' will be removed, whereas unselected members (e.g., 236B'' of FIG. 2N) of capped semiconductor fins 236B' and unselected members (e.g., 236A'' of FIG. 2P) of capped semiconductor fins 236A' will remain.

In FIG. 2N, hard masks 242 are formed so that unselected members 236B'' of capped semiconductor fins 236B' and instances of capped semiconductor fins 236A' adjacent to unselected members 236B'' (hereinafter, adjacent instances 236A') are covered by hard masks 242, which produces an intermediate structure 245.

In intermediate structure 245, selected members 236B''' of capped semiconductor fins 236B', some instances of capped semiconductor fins 236A' and some areas of STI regions 240 are exposed. In some embodiments, hard masks 242 are the residual portions of a photoresist layer which has been subjected to patterning. In some embodiments, layer 214 is formed using a spin-coating process and soft baking process. In some embodiments, the photoresist layer is exposed to radiation using a mask. The exposed photoresist layer is developed using post-exposure baking (PEB), developing, and hard baking thereby forming a patterned photoresist layer. In some embodiments, selected portions of the patterned photoresist layer are removed using a suitable process, such as wet stripping or plasma ashing.

In FIG. 2O, intermediate structure 245 is etched with a fifth etchant appropriate to etch sensitivity ES216' of cap 216'.

STI regions 240 and caps 208' of capped semiconductor fins 236A' are unaffected by the fifth etchant. In some embodiments, STI regions 240 and caps 208' of capped semiconductor fins 236A' are substantially unaffected by the fifth etchant. While some portion of STI regions 240 and/or some portion of caps 208' of capped semiconductor fins 236A' might be removed by the fifth etchant, nevertheless the corresponding removed portions are regarded as insignificant because sufficient portions of STI regions 240 and/or sufficient portions of caps 208' of capped semiconductor fins 236A' remain such that STI regions 240 and/or capped semiconductor fins 236A' protect the corresponding underlying structures from the fifth etchant. Hence, STI regions 240 and caps 208' of capped semiconductor fins 236A' are regarded as being substantially unaffected by the fifth etchant.

In some embodiments, relative to the fifth etchant (ET5), etch sensitivity ES216' of caps 216' (ES$216'_{ET5}$) of selected members 236B" of capped semiconductor fins 236B' is at least twice as great as etch sensitivity ES240 of STI regions 240 (ES$240_{ET5}$) such that $$2*ES240_{ET5} \leq ES216'_{ET5},$$

and etch sensitivity ES216' of caps 216' is at least twice as great as etch sensitivity ES208' of caps 208' (ES$208'_{ET5}$) of capped semiconductor fins 236A' such that $$2*ES208'_{ET5} \leq ES216'_{ET5}.$$

As a result, caps 216' of selected members 236B" of capped semiconductor fins 236B' are removed, which leaves exposed regions 216" of semiconductor fins 238B. Also as a result, the second set of capped semiconductor fins 236B' is reduced to include only unselected members 236B". In some embodiments, the fifth etchant used in the context of FIG. 2O is the same as the second etchant used in the context of FIG. 2K. In some embodiments, the etching process includes applying a dry (or plasma) etch to remove caps 216' of selected members 236B" of capped semiconductor fins 236B'. In some embodiments, the etching process includes applying a wet etch with a hydrofluoric acid (HF) solution to remove caps 216' of selected members 236B" of capped semiconductor fins 236B'.

Also in FIG. 2O, after having exposed intermediate structure 245 to the fifth etchant, hard masks 242 are removed. In some embodiments, hard masks 242 are removed using a suitable process, such as wet stripping or plasma ashing.

Extending the spans of hard masks 242 so that hard masks 242 cover adjacent instances 236A' ensures that hard masks 242 fully cover unselected members 236B" of capped semiconductor fins 236B'. As a practical matter, near-wavelength and sub-wavelength photolithography enable locating capped semiconductor fins 236A' and 236B' so closely together (relative to reference direction 217) that the tolerance of (amount of variation in the accuracy of) the mask-alignment process is unacceptably large. Accordingly, if one were to attempt to limit the spans of hard masks 242 to cover only unselected members 236B" of capped semiconductor fins 236B', then the tolerance in the mask-alignment process would result in misalignment at the edges of hard masks 242 such that some of unselected members 236B" would not be fully covered. Such misalignment is called out by reference 244 in FIG. 2N albeit in the context of misalignment with respect to adjacent instances 236A' (as discussed below).

Such misalignment would cause the partially covered unselected members 236B" to be partially etched, which would lead to an unwanted increase in the variation in thickness $T_{Si}$ of instances of unselected members 236B".

Instead, by extending the spans of hard masks 242 so that not only unselected members 236B" are covered but also adjacent instances 236A', then adjacent instances 236A' align with the edges of hard masks 242 such that only adjacent instances 236A' suffer misalignment 244 with the edges of hard masks 242. Similar to caps 208' of all capped semiconductor fins 236A', because caps 208' of adjacent instances 236A' are unaffected by the fifth etchant, the misalignment does not result in unwanted etching of the partially uncovered adjacent instances 236A'. In some embodiments, caps 208' of adjacent instances 236A' are substantially unaffected by the fifth etchant. As a beneficial result, variation in thickness $T_{Si}$ of instances of unselected members 236B" is reduced.

In FIG. 2P, hard masks 246 are formed, which results in an intermediate structure 247.

In intermediate structure 247, unselected members 236A" of capped semiconductor fins 236A' and instances of capped semiconductor fins 236B' adjacent to unselected members 236A" (hereinafter, adjacent instances 236B') and some instances of exposed regions 216" of semiconductor fins 238B adjacent to unselected members 236A" (hereinafter, adjacent fins 238B) are covered by hard masks 246. Also in intermediate structure 247, selected members 236A''' of capped semiconductor fins 236A', some instances of capped semiconductor fins 236B' and some areas of STI regions 240 are exposed. In some embodiments, hard masks 246 are formed in a manner similar to how hard masks 242 are formed.

In FIG. 2Q, intermediate structure 247 is etched with a sixth etchant appropriate to etch sensitivity ES208' of cap 208'.

STI regions 240 and caps 216' of capped semiconductor fins 236B' are unaffected by the sixth etchant. In some embodiments, STI regions 240 and caps 216' of capped semiconductor fins 236B' are substantially unaffected by the sixth etchant. 'Substantially unaffected' with respect to the sixth etchant is understood similarly to how 'substantially unaffected' is understood with respect to the fifth etchant (as discussed above). While some portion of STI regions 240 and/or some portion of caps 216' of capped semiconductor fins 236B' might be removed by the sixth etchant, nevertheless the corresponding removed portions are regarded as insignificant because sufficient portions of STI regions 240 and/or sufficient portions of caps 216' of capped semiconductor fins 236B' remain such that STI regions 240 and/or caps 216' protect the corresponding underlying structures from the sixth etchant. Hence, STI regions 240 and caps 216' of capped semiconductor fins 236B' are regarded as being substantially unaffected by the sixth etchant. Additional uses of the term "substantially unaffected" with respect to other etchants follow and should be understood similarly.

In some embodiments, relative to the sixth etchant (ET6), etch sensitivity ES208' of caps 208' (ES$208'_{ET6}$) of selected members 236A''' of capped semiconductor fins 236A' is at least twice as great as etch sensitivity ES240 of STI regions 240 (ES$240_{ET6}$) such that $$2*ES240_{ET6} \leq ES208'_{ET6},$$

and etch sensitivity ES208' of caps 208' is at least twice as great as etch sensitivity ES216' of caps 216' (ES$216'_{ET6}$) of capped semiconductor fins 236B' such that $$2*ES216'_{ET6} \leq ES208'_{ET6}.$$

As a result, caps 208' of selected members 236A''' of capped semiconductor fins 236A' are removed, which leaves exposed regions 208" over semiconductor fins 238A. Also as a result, the first set of capped semiconductor fins 236A' is reduced to include only unselected members 236A". Also in FIG. 2Q, after having exposed intermediate structure 247 to the sixth etchant, hard masks 246 are removed, which produces an intermediate structure 249. In some embodiments, the sixth etchant used in the context of FIG. 2Q is the same as the first etchant used in the context of FIG. 2K. In some embodiments, intermediate structure 247 is etched in a manner similar to how intermediate structure 245 is etched albeit with etchant appropriate to etch sensitivity ES208' of cap 208'.

Similar to hard masks 242, the spans of hard masks 246 are extended so that hard masks 246 cover adjacent instances 236B' so as to ensure that hard masks 246 fully cover unselected members 236A" of capped semiconductor fins 236A'. Similar to caps 216' of all capped semiconductor fins 236B', because caps 216' of adjacent instances 236B' are unaffected by the sixth etchant, misalignment 248 does not result in unwanted etching of the partially uncovered adjacent instances 236B'. In some embodiments, caps 216' of adjacent instances 236B' are substantially unaffected by the sixth etchant. As a beneficial result, variation in thickness $T_{Si}$ of instances of unselected members 236A" is reduced.

In FIG. 2R, intermediate structure 249 is exposed to a seventh etchant appropriate to semiconductor fins 238A and 238B exposed in corresponding regions 208" and 216". As a result, the height of semiconductor fins 238A and 238B in corresponding regions 208" and 216" is reduced.

In some embodiments, the height of semiconductor fins 238A and 238B in corresponding regions 208" and 216" is reduced by performing a trench-etch to etch the exposed portions of semiconductor fins 238A and 238B. In some embodiments, the seventh etchant used in the context of FIG. 2R is the same as the fourth etchant used in the context of FIG. 2K. In some embodiments, the height of semiconductor fins 238A and 238B in corresponding regions 208" and 216" is reduced so that the heights of semiconductor fins 238A and 238B in corresponding regions 208" and 216" are approximately the same as the height of substrate 200.

In FIG. 2S, STI regions 240 are removed.

In some embodiments, STI regions 240 are removed using a wet dip. In some embodiments, the wet dip is a diluted hydrofluoric (HF) acid solution. In some embodiments, STI regions 240 are removed using dry etching.

In some embodiments, the portion of FIG. 2S to the left of cell boundary 202 in FIG. 2S represents a cell including inchoate 2-fin thin film transistors (TFTs); and the portion of FIG. 2S to the right of cell boundary 202 in FIG. 2S represents a cell including inchoate 1-fin TFTs. Here, the 2-fin TFTs and the 1-fin TFTs are referred to as inchoate because only fins 238A and 238B of the yet-to-be-formed TFTs are present in FIG. 2S. In some embodiments, TFTs including other numbers of fins are contemplated.

FIGS. 3A-3V are cross-sections of other various stages in the manufacture of fins for a semiconductor device which includes Fin-FETs in accordance with at least one embodiment of the present disclosure.

In contrast to FIGS. 2A-2S (which, among other things, use two mandrels—the first being shown in FIG. 2A and the second being shown in FIG. 2F), FIGS. 3A-3V use one mandrel (shown in FIG. 3A, as discussed below).

In some embodiments, FIGS. 3A-3N correspond to block 104 of FIG. 1, where FIG. 3N is the result of block 104, and FIGS. 3O-3V correspond to block 106 of FIG. 1, where FIG.

3V is the result of block 106. In some embodiments, FIGS. 3A-3O correspond to block 104 of FIG. 1, where FIG. 3O is the result of block 104, and FIGS. 3P-3V correspond to block 106 of FIG. 1, where FIG. 3V is the result of block 106. In some embodiments, FIGS. 3A-3P correspond to block 104 of FIG. 1, where FIG. 3P is the result of block 104, and FIGS. 3Q-3V correspond to block 106 of FIG. 1, where FIG. 3V is the result of block 106.

In FIG. 3A, first mandrel features 304 are built on a semiconductor substrate 300, which results in an intermediate structure 301. In some embodiments, substrate 300 is formed in a manner similar to how substrate 200 is formed.

In intermediate structure 301, first regions 306 of substrate 300 are exposed. In some embodiments, first mandrel features 304 are built in a manner similar to how first mandrel features 204 of FIG. 2A and second mandrel features 218 of FIG. 2F are built. In some embodiments, the fins that result from the various stages of manufacture of FIGS. 3A-3V are incorporated in a semiconductor device which includes Fin-FETs, with at least some of the fins being included in SRAM memory cells. In such embodiments, dashed line 302 represents a border between adjacent SRAM memory cells.

In some embodiments, structures 304 are not mandrels but instead are spacers. In some embodiments, spacers 304 result from three preliminary stages. In the first preliminary stage, a preliminary-mandrel is built on substrate 300 in a mandrel region corresponding to the region between spacers 304 (e.g., in a manner similar to how first mandrel features 204 of FIG. 2A and second mandrel features 218 of FIG. 2F are built). In the second preliminary stage, spacers 304 are built on portions of substrate 300 (e.g., in a manner similar to how first spacers 208 FIG. 2B, second spacers 222 of FIG. 2G and third spacers 228 of FIG. 2I are built) such that spacers 304 abut sidewalls of the preliminary-mandrel. In the third preliminary stage, the preliminary-mandrel is removed (e.g., in a manner similar to how first mandrel features 204 of FIG. 2C and second mandrel features 218 of FIG. 2H are removed).

In FIG. 3B, first spacers 308 on substrate 300 are built in some areas of first regions 306, which leaves second regions 310 of substrate 300 exposed.

First spacers 308 abut sidewalls of first mandrel features 304. In some embodiments, first spacers 308 are built in a manner similar to how first spacers 208 FIG. 2B, second spacers 222 of FIG. 2G and third spacers 228 of FIG. 2I are built. In FIG. 3C, first mandrel features 304 are removed, which leaves third regions 312 of substrate 300 exposed. In some embodiments, first mandrel features 304 are removed in a manner similar to how first mandrel features 204 of FIG. 2C and second mandrel features 218 of FIG. 2H are removed.

In FIG. 3D, second spacers 314 are built on substrate 300 in some areas of third regions 312.

Second spacers 314 abut sidewalls of first spacers 308. Second spacers 314 have an etch sensitivity, ES314. In some embodiments, second spacers 314 are built in a manner similar to how first spacers 308 are built.

In FIG. 3E, first spacers 308 are removed, which leaves fourth regions 316 of substrate 300 exposed.

In some embodiments, first spacers 308 are removed by etching. In some embodiments, the etching process is a wet etching, a dry etching, or a combination thereof.

In FIG. 3F, third spacers 318 are built on substrate 300 in some areas of fourth regions 316, which leaves fifth regions 320 of substrate 300 exposed.

Third spacers 318 abut sidewalls of second spacers 314. Third spacers 318 have an etch sensitivity, ES318, with etch sensitivity ES318 being different than etch sensitivity ES314. In some embodiments, third spacers 318 are built in a manner similar to how first spacers 308 are built.

In FIG. 3G, a layer 322 of first etch stop material is deposited on second spacers 314 and fifth regions 320 of substrate 300.

In some embodiments, layer 322 is formed in a manner similar to how layer 214 of FIG. 2D is formed.

In FIG. 3H, a portion of layer 322 is removed, which leaves first etch stop layer (ESL) portions 324 on substrate 300, which produces an intermediate structure 326.

First ESL portions 324 abut sidewalls of third spacers 318. First ESL portions 324 have an etch sensitivity, ES324, with etch sensitivity ES324 being different than etch sensitivity ES314 and etch sensitivity ES318. In some embodiments, relative to a reference direction 317 parallel to a plane of the substrate, widths of second spacers 314 and first ESL portions 324 are approximately (if not nearly exactly) the same. In some embodiments, first ESL portions 324 are formed in a manner similar to how ESL portions 216 of FIG. 2E are formed.

In FIG. 3I, portions of second spacers 314 and first ESL portions 324 are removed, which results in an intermediate structure 326''.

Intermediate structure 326'' includes reduced height versions 314' of second spacers 314 and reduced height versions 324' of first ESL portions 324. In some embodiments, intermediate structure 326 is etched with a second etchant appropriate to etch sensitivity ES324 of first ESL portions 324, which results in an intermediate structure 326' (not shown). Second spacers 314 and third spacers 318 are unaffected by the second etchant. In some embodiments, second spacers 314 and third spacers 318 are substantially unaffected by the second etchant. In some embodiments, relative to the second etchant (ET2), etch sensitivity ES324 of first ESL portions 324 (ES324$_{ET2}$) is at least twice as great as etch sensitivity ES318 of third spacers 318 (ES318$_{ET2}$) such that $$2*ES318_{ET2} \leq ES324_{ET2},$$

and etch sensitivity ES324 of first ESL portions 324 is at least twice as great as etch sensitivity ES314 of second spacers 314 (ES314$_{ET2}$) such that $$2*ES314_{ET2} \leq ES324_{ET2}.$$

As a result, portions of first ESL portions 324 are removed, leaving first ESL portions 324'.

Then, intermediate structure 326' (again, not shown) is etched with a first etchant appropriate to etch sensitivity ES314 of second spacers 314, which results in intermediate structure 326''. First ESL portions 324' and third spacers 318 are unaffected by the first etchant. In some embodiments, first ESL portions 324' and third spacers 318 are substantially unaffected by the first etchant. In some embodiments, relative to the first etchant (ET1), etch sensitivity ES314 of second spacers 314 (ES314$_{ET1}$) is at least twice as great as etch sensitivity ES318 of third spacers 318 (ES318$_{ET1}$) such that $$2*ES318_{ET1} \leq ES314_{ET1},$$

and etch sensitivity ES314 of second spacers 314 is at least twice as great as etch sensitivity ES324 of first ESL portions 324' (ES324'$_{ET1}$) such that $$2*ES324'_{ET1} \leq ES314_{ET1}.$$

As a result, portions of second spacers 314 are removed, leaving second spacers 314'. In some embodiments, the order in which the first and second etchants are applied is reversed such that the first etchant is applied and then the second etchant is applied.

In FIG. 3J, a layer 327 of second ESL material is deposited on second spacers 314', first ESL portions 324' and third spacers 318. In some embodiments, layer 327 is formed in a manner similar to how layer 322 is formed.

In FIG. 3K, a portion of layer 327 is removed, which leaves second ESL portions 328 and which produces an intermediate structure 330.

Second ESL portions 328 have an etch sensitivity, ES328, with etch sensitivity ES328 being different than etch sensitivity ES314, etch sensitivity 324 and etch sensitivity ES318. In some embodiments, heights of second ESL portions 328 are the same as heights of third spacers 318. In some embodiments, second ESL portions 328 are formed in a manner similar to how first ESL portions 324 are formed.

In FIG. 3L, third spacers 318 are removed, which leaves sixth regions 331 of substrate 300 exposed.

In some embodiments, third spacers 318 are removed by etching. In some embodiments, the etching process is a wet etching, a dry etching, or a combination thereof. In some embodiments, intermediate structure 330 is etched with a third etchant appropriate to etch sensitivity ES318 of third spacers 318. Second ESL portions 328 are substantially unaffected by the third etchant. In some embodiments, second ESL portions 328 are substantially unaffected by the first etchant. In some embodiments, relative to the third etchant (ET3), etch sensitivity ES318 of third spacers 318 (ES318$_{ET3}$) is at least twice as great as etch sensitivity ES328 of second ESL portions 328 (ES328$_{ET3}$) such that $$2*ES328_{ET3} \leq ES318_{ET3}.$$

In FIG. 3M, second ESL portions 328 are etched to reduce the widths of second ESL portions 328 (and thereby produce second ESL portions 328') while having little (if any) negative effect on the heights of second ESL portions 328, which results in an intermediate structure 333. Ultimately, the widths of semiconductor fins 338A and 338B correspond to the resultant width of second ESL portions 328'. Hence, the width of second ESL portions 328' determines the widths of semiconductor fins 338A and 338B.

In intermediate structure 333, some areas of second spacers 314', some areas of first ESL portions 324' and sixth regions 332 of substrate 300 are left exposed. In some embodiments, the etching is anisotropic etching. In some embodiments, the anisotropic etching is a plasma etching. In some embodiments, both widths and heights of second ESL portions 328 are reduced.

In FIG. 3N, the exposed areas of second spacers 314', the exposed areas of first ESL portions 324', a layer of substrate 300 in sixth regions 332, a layer of substrate 300 under the exposed areas of second spacers 314' and a layer of substrate 300 under the exposed areas of the first ESL portions 324' are removed, which results in an intermediate structure 333'.

In intermediate structure 333'', seventh regions 334 are left exposed, and inchoate versions 336A and 336B of capped semiconductor fins 336A' and 336B' are formed. Here, because second ESL portions 328' remain, versions 336A and 336B are referred as inchoate. In some embodiments, the exposed areas of second spacers 314', the exposed areas of first ESL portions 324' and sixth regions 332 of substrate 300 are removed in a multi-step etching process. In some embodiments, the multi-step etching process includes at least three steps. In the first step, intermediate structure 333 is etched with a fourth etchant appropriate to an etch sensitivity ES314' of second spacers 314', where ES314'=ES314, which results in an intermediate structure 333' (not shown), with the remainders of second spacers 314' being referred to hereafter as caps 314". In the second step, intermediate structure 333' is etched with a fifth etchant appropriate to an etch sensitivity ES324' of first ESL portions 324', where ES324'=ES324, which results in an intermediate structure 333" (not shown), with the remainders of first ESL portions 324' being referred to hereafter as caps 324". In the third step, intermediate structure 333" is etched with a sixth etchant appropriate to an etch sensitivity ES300 of substrate 300, which results in an intermediate structure 237". In some embodiments, the order of the first and second etching steps is reversed. In some embodiments, each of the first and second etching steps etch substrate 200, thus eliminating a need for the third etching steps. In some embodiments, the six etchants (namely, the first, second, third, fourth, fifth and sixth etchants) are selected from the group consisting of HF, HNO3, H2SO4 and NH4OH, with the determination of which etchant to be used as the first, second, third, fourth, fifth and sixth etchants depending upon the material to be etched. In some embodiments, etching can be implemented using inductively coupled plasma (ICP) etching, reactive-ion etching (RIE) or another suitable etching process, which are controlled in part by tuning the input gases, e.g., CF4, Ar, O2, Cl2, CF3I, NH3 or other suitable gases.

In FIG. 3O, STI regions 340 are formed in seventh regions 334 of substrate 300.

STI regions 340 abut sidewalls of inchoate versions 336A and 336B of capped semiconductor fins 336A' and 336B'. In some embodiments, STI regions 340 are formed in a manner similar to how STI regions 240 of FIG. 2M are formed.

In FIG. 3P, second ESL portions 328' and portions of STI regions 340 are removed, which exposes caps 314" and 324" of corresponding capped semiconductor fins 336A' and 336B', and which produces an intermediate structure 341.

Intermediate structure 341 is an example of a structure that includes a semiconductor substrate (namely, substrate 300) and a plurality of capped semiconductor fins (namely, capped semiconductor fins 336A' and 336B'). In some embodiments, CMP is performed to remove second ESL portions 328' and excess portions of STI material in seventh regions 334 of substrate 300 and thereby expose caps 314" and 324" of corresponding capped semiconductor fins 336A' and 336B'. Caps 314" have an etch sensitivity ES314", where ES314"=ES314'. Caps 324" have an etch sensitivity ES324", where ES324"=ES324'. In some embodiments, the CMP provides an approximately planar surface. In some alternative embodiments, no STI regions are formed.

After reaching the stage of FIG. 3P, over the course of subsequent stages of FIGS. 3Q-3S, selected members (e.g., 336B'" of FIG. 3Q) of capped semiconductor fins 336B' and selected members (e.g., 336A'" of FIG. 3S) of capped semiconductor fins 336A' will be removed.

In FIG. 3Q, hard masks 342 are formed so that unselected members 336B" of capped semiconductor fins 336B' and instances of capped semiconductor fins 336A' adjacent to unselected members 336B" (hereinafter, adjacent instances 336A') are covered by hard masks 342, which produces an intermediate structure 345.

In intermediate structure 345, selected members 336B'" of capped semiconductor fins 336B', some instances of capped semiconductor fins 336A' and some areas of STI regions 340' are exposed. In some embodiments, hard masks 342 are formed in a manner similar to how hard masks 242 of FIG. 2N are formed.

In FIG. 3R, intermediate structure 345 is etched with a seventh etchant appropriate to etch sensitivity ES324' of cap 324'.

STI regions 340' and caps 314" of capped semiconductor fins 336A' are unaffected by the seventh etchant. In some embodiments, STI regions 340' and caps 314" of capped semiconductor fins 336A' are substantially unaffected by the seventh etchant. In some embodiments, relative to the seventh etchant (ET7), etch sensitivity ES324" of caps 324" (ES324'$_{ET7}$) is at least twice as great as an etch sensitivity ES340' of STI regions 340' (ES340'$_{ET7}$) such that $$2*ES340'_{ET7} \leq ES324"_{ET7},$$

and etch sensitivity ES324" of caps 324" is at least twice as great as etch sensitivity ES314' of caps 314" (ES314"$_{ET7}$) such that $$2*ES314"_{ET7} \leq ES324"_{ET7}.$$

As a result, caps 324" of selected members 336B'" of capped semiconductor fins 336B' are removed, which leaves exposed regions 324" of semiconductor fins 338B. Also as a result, the second set capped semiconductor fins 336B' is reduced to include only unselected members 336B". In some embodiments, the seventh etchant used in the context of FIG. 3R is the same as the fifth etchant used in the context of FIG. 3N. In some embodiments, the etching process is similar to the etching process used in the context of FIG. 2O.

Also in FIG. 3R, after having exposed intermediate structure 345 to the seventh etchant, hard masks 342 are removed. In some embodiments, hard masks 342 are removed using a suitable process, such as wet stripping or plasma ashing.

Extending the spans of hard masks 342 so that hard masks 342 cover adjacent instances 336A' ensures that hard masks 342 fully cover unselected members 336B" of capped semiconductor fins 336B'. As a practical matter, near-wavelength and sub-wavelength photolithography enable locating capped semiconductor fins 336A' and 336B' so closely together (relative to reference direction 343) that the tolerance of (amount of variation in the accuracy of) the mask-alignment process is unacceptably large. Accordingly, if one were to attempt to limit the spans of hard masks 342 to cover only unselected members 336B" of capped semiconductor fins 336B', then the tolerance in the mask-alignment process would result in misalignment at the edges of hard masks 342 such that some of unselected members 336B" would not be fully covered. Such misalignment is called out by reference 344 in FIG. 3Q albeit in the context of misalignment with respect to adjacent instances 336A' (as discussed below). Such misalignment would cause the partially covered unselected members 336B" to be partially etched, which would lead to an unwanted increase in the variation in thickness $T_{Si}$ of instances of unselected members 336B".

Instead, by extending the spans of hard masks 342 so that not only unselected members 336B" are covered but also adjacent instances 336A', then adjacent instances 336A' align with the edges of hard masks 342 such that only adjacent instances 336A' suffer misalignment 344 with the edges of hard masks 342. Similar to caps 314" of all capped semiconductor fins 336A', because caps 314" of adjacent instances 336A' are unaffected by the seventh etchant, the misalignment does not result in unwanted etching of the partially uncovered adjacent instances 336A'. In some embodiments, caps 314" of adjacent instances 336A' are substantially unaffected by the seventh etchant. As a beneficial result, variation in thickness $T_{Si}$ of instances of unselected members 336B" is reduced.

In FIG. 3S, hard masks 346 are formed, which produces an intermediate structure 347.

In intermediate structure 347, unselected members 336A" of capped semiconductor fins 336A', some instances of capped semiconductor fins 336B' adjacent to unselected members 336A" (hereinafter, adjacent instances 336B') and some instances of exposed regions 324" of semiconductor fins 338A adjacent to unselected members 336A" (hereinafter, adjacent fins 338A) are covered by hard masks 344. Also in intermediate structure 347, selected members 336A''' of capped semiconductor fins 336A', some instances of capped semiconductor fins 336B', some instances of exposed regions 324" of semiconductor fins 338A, and some areas of STI regions 340 are exposed. In some embodiments, hard masks 346 are formed in a manner similar to how hard masks 342 are formed.

In FIG. 3T, intermediate structure 347 is etched with an eighth etchant appropriate to etch sensitivity ES314' of cap 314'.

STI regions 340, caps 324" of capped semiconductor fins 336B' and semiconductor fins 338A are unaffected by the eighth etchant. In some embodiments, STI regions 340 and caps 324" of capped semiconductor fins 336B' are substantially unaffected by the eighth etchant. In some embodiments, relative to the eighth etchant (ET8), etch sensitivity ES314' of caps 314" (ES314'$_{ET8}$) is at least twice as great as etch sensitivity ES340' of STI regions 340' (ES340'$_{ET8}$) such that $$2*ES340'_{ET8} \leq ES314'_{ET8},$$

and etch sensitivity ES314' of caps 314" is at least twice as great as etch sensitivity ES324' of caps 324" (ES324"$_{ET8}$) such that $$2*ES324"_{ET8} \leq ES314'_{ET8}.$$

As a result, caps 314" of selected members 336A''' of capped semiconductor fins 236A' are removed, which leaves exposed regions 314''' over semiconductor fins 338. Also as a result, the first set of capped semiconductor fins 336A' is reduced to include only unselected members 336A". In some embodiments, the eighth etchant used in the context of FIG. 3T is the same as the fourth etchant used in the context of FIG. 3N. In some embodiments, the etching process is similar to the etching process used in the context of FIG. 2Q.

Also in FIG. 3T, after having exposed intermediate structure 347 to the eighth etchant, hard masks 346 are removed, which produces an intermediate structure 349. In some embodiments, hard masks 346 are removed using a suitable process, such as wet stripping or plasma ashing.

Like hard masks 342, the spans of hard masks 346 are extended so that hard masks 346 cover adjacent instances 336B' so as to ensure that hard masks 346 fully cover unselected members 336A" of capped semiconductor fins 336A'. Similar to caps 324" of all capped semiconductor fins 336B', because caps 324" of adjacent instances 336B' are unaffected by the eighth etchant, misalignment 348 does not result in unwanted etching of the partially uncovered adjacent instances 336B'. In some embodiments, caps 324" of adjacent instances 336B' are substantially unaffected by the eighth etchant. As a beneficial result, variation in thickness $T_{Si}$ of instances of unselected members 336A" is reduced.

In FIG. 3U, intermediate structure 349 is exposed to a ninth etchant appropriate to semiconductor fins 338A and 338B exposed in corresponding regions 314" and 324". As a result, the heights of semiconductor fins 338A and 338B in exposed in regions 314" and 324" are reduced, which results in an intermediate structure 352.

In some embodiments, the height of semiconductor fins 338A and 338B in corresponding regions 314" and 324" is reduced by performing a trench-etch to etch the exposed portions of semiconductor fins 338A and 338B. In some embodiments, the ninth etchant used in the context of FIG. 3U is the same as the sixth etchant used in the context of FIG. 3N. In some embodiments, the heights of semiconductor fins 338A and 338B in exposed in regions 314" and 324" are reduced so as not to stand proud of substrate 300 (the heights of semiconductor fins 338A and 338B in exposed in regions 314" and 324" are approximately the same as the height of substrate 300).

In FIG. 3V, STI regions 340 are removed, which results in an intermediate structure 354.

In some embodiments, STI regions 340 are removed using a wet dip. In some embodiments, the wet dip is a diluted hydrofluoric (HF) acid solution. In some embodiments, STI regions 340 are removed using dry etching.

In some embodiments: the portion of intermediate structure 354 to the left of cell boundary 302 in FIG. 3V represents a cell including inchoate 2-fin thin film transistors (TFTs); and the portion of FIG. 3V to the right of cell boundary 302 in FIG. 3V represents a cell including inchoate 1-fin TFTs. Here, the 2-fin TFTs and the 1-fin TFTs are referred to as inchoate because only fins 338A and 338B of the yet-to-be-formed TFTs are present in FIG. 3V.

Figure 4A:
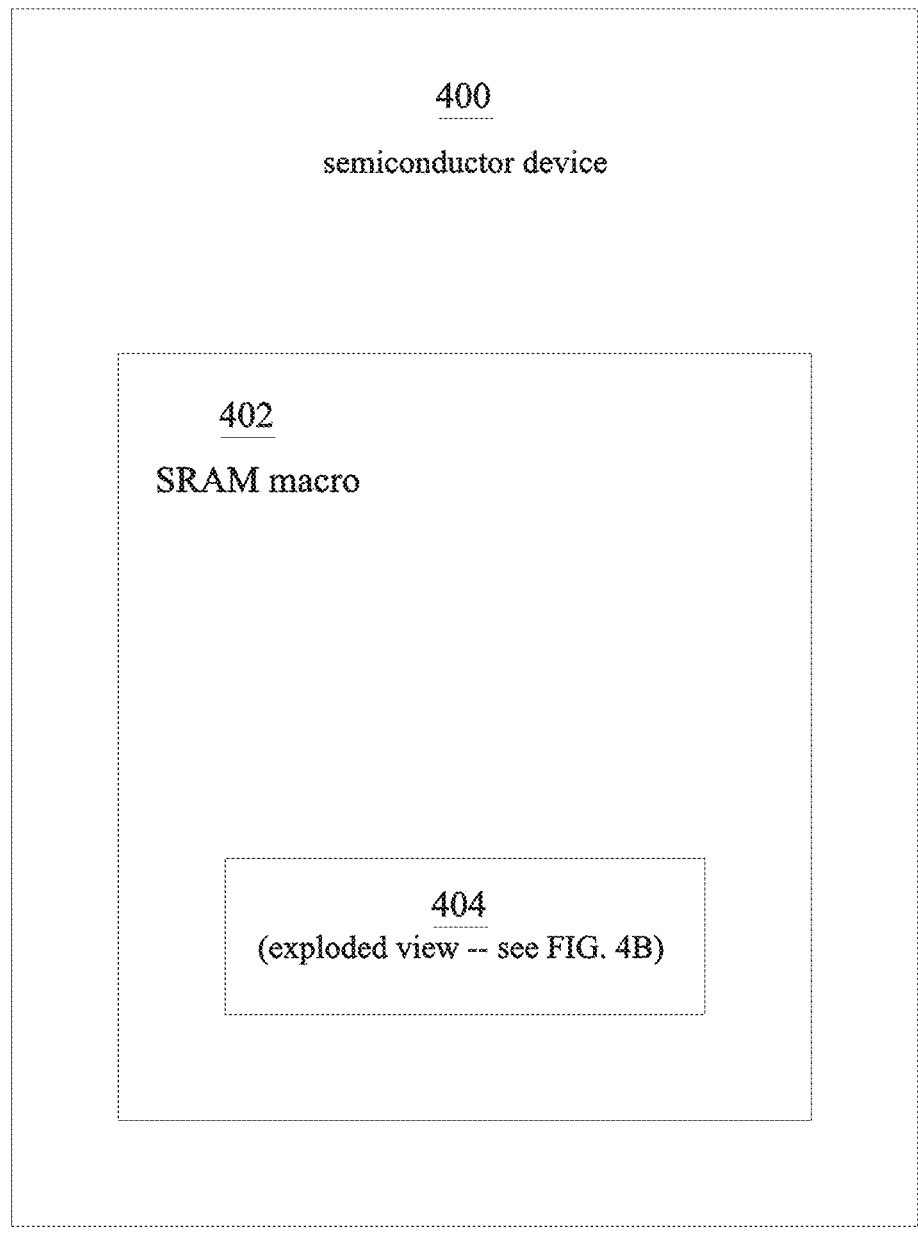
FIG. 4A is a block diagram of a semiconductor device in accordance with at least one embodiment of the present disclosure.

FIG. 4A is a block diagram of a semiconductor device 400 in accordance with at least one embodiment of the present disclosure.

In FIG. 4A, semiconductor device 400 includes, among other things, an SRAM macro 402. SRAM macro 402 includes a group 404 of SRAM cells. In some embodiments, the SRAM cells of group 404 includes TFT's formed according to FIG. 1 and FIGS. 2A-2S or FIG. 1 and FIGS. 3A-3V.

Figure 4B:
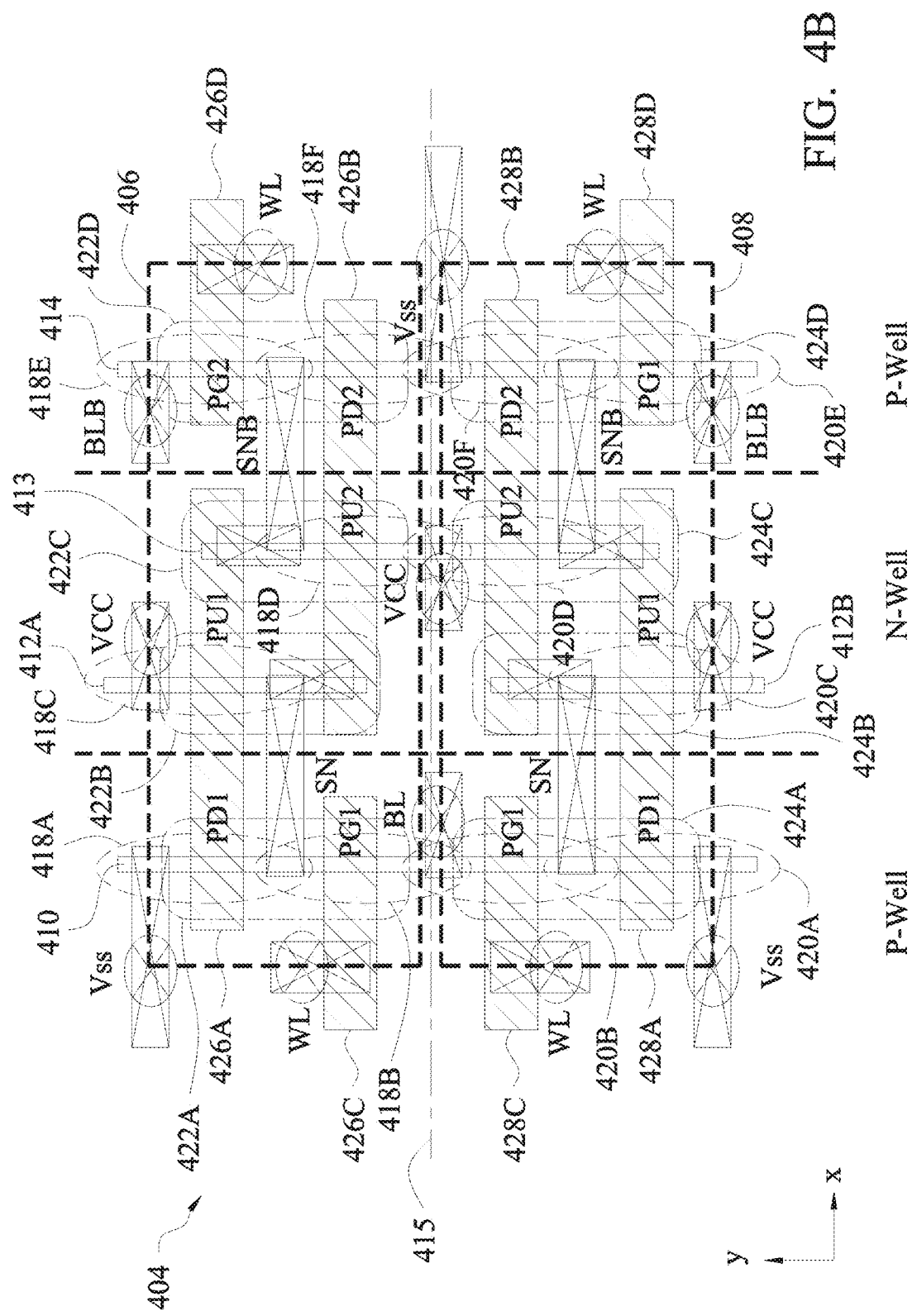
FIG. 4B is an exploded view of a part of the semiconductor device of FIG. 4A in accordance with at least one embodiment of the present disclosure.

FIG. 4B is an exploded view of a part of semiconductor device 400 of FIG. 4A in accordance with at least one embodiment of the present disclosure.

More particularly, FIG. 4B is a layout diagram of two adjacent SRAM cells 406 and 408 included within 404 of FIG. 4A, arranged together to form an array. In some embodiments, each of SRAM cells 406 and 408 includes six transistors. In particular, SRAM cell 406 includes transistors 418A-418F, and SRAM cell 408 includes transistors 420A-420F. SRAM macro 402 includes a group 404 of SRAM cells. In some embodiments, transistors 418A-418F, and SRAM cell 408 that includes transistors 420A-420F are formed according to FIG. 1 and FIGS. 2A-2S or FIG. 1 and FIGS. 3A-3V. In some embodiments, the instances of a given cell layout are flipped or rotated relative to one another in order to facilitate higher packing densities. In some embodiments, SRAM cell 408 includes the same components as SRAM cell 406 but, relative to an imaginary reference line 415 parallel to the X axis, components in SRAM 408 are mirror symmetric with respect to corresponding components in SRAM cell 406.

In FIG. 4B, there are four fins, 410, 412 (shown as 412A and 412B), 413 and 414. Fins 410 and 414 are unitary structures that overlap and extend beyond SRAM cells 406 and 408. Fin 413 is a unitary structure that overlaps portions of SRAM cells 406 and 408. Fins 412A and 412B are collinear and represent segments of a formerly unitary structure. Fin 412A overlaps a portion of SRAM cell 406. Fin 412B overlaps a portion of SRAM 408.

Also in FIG. 4B, there are four active areas. In particular, SRAM cell 406 includes active regions 422A-422D aligned with corresponding fins 410, 412A, 413 and 414. SRAM cell 408 includes active regions 424A-424D aligned with corresponding fins 410, 412B, 413 and 414. The active regions extend parallel in a y-direction shown in FIG. 4B across the width of the SRAM cell 406. The gate regions extend parallel in the x-direction shown in FIG. 4B along the length of SRAM cell 406. In addition, the fin lines are orthogonal to the gate regions in the layout diagram. A transistor is formed at a cross point of a fin line and a gate region. As shown in FIG. 4B, the six transistors of each of SRAM cells 406 and 408 are formed at different cross points. For example, a first pass-gate transistor is formed at the cross point between a first fin 410 and a gate region labeled as PG1.

Two vertical dashed lines that intersect SRAM cells 406 and 408 indicate boundaries between a p-type well in the substrate and an n-type well in the substrate in which respective fin transistors are formed. In some embodiments, a drain/source region of a fin transistor is generally doped an opposite dopant type from the dopant type of the well in which the drain/source region is formed. In some embodiments, a source/drain region of a fin-FET is generally p-type doped when the well in which the active area is formed is an n-type well.

Also in FIG. 4B, the active areas of transistors PG1 and PD1 is formed in a p-type well. As a result, these transistors are n-type transistors. The active areas of transistors PU1 and PU2 are formed in an n-type well. As a result, these transistors are p-type transistors. The active areas of transistors PD2 and PG2 are formed in a p-type well. Similarly, these transistors are n-type transistors.

Yet also in FIG. 4B, a conductive structure 426A is used as gates of corresponding transistors 418A and 418C. A conductive structure 426B is used as gates of corresponding transistors 418D and 418F. A conductive structure 428A is used as gates of corresponding transistors 420A and 420C. A conductive structure 428B is used as gates of corresponding transistors 420D and 420F. In this manner, each of conductive structures 426A, 426B, 428A and 428B electrically couples the gates of the corresponding two transistors. A single conductive structure 426C is dedicated to transistor 418B. A single conductive structure 426D is dedicated to transistor 418E. A single conductive structure 428C is dedicated to transistor 420B. A single conductive structure 428D is dedicated to transistor 420E. In some embodiments, the conductive structures 426C, 426D, 428C and 428D extend beyond the corresponding cell boundaries so that the conductive structures are shared by corresponding adjacent SRAM cells (not shown).

In some embodiments, various contacts and their corresponding interconnect vias are employed to couple components in SRAM cell 406. Through a via and a gate contact, word line contacts WL are coupled to corresponding conductive structures 426C, 426D, 428C and 428D. A bit line contact BL is coupled to drains of transistors 418B and 420B. Complementary bit line contacts BLB are coupled to drains of corresponding transistors 418E and 420E.

Power source contacts VCC are coupled to sources of corresponding transistors 418C and 420C. Ground contacts VSS are coupled to sources of transistors 418A and 420A. A storage node contact SN couples together the drains of transistors 418A, 418B and 418C. Another storage node contact SN couples together the drains of transistors 420A, 420B and 420C. A storage node contact SNB couples together the drains of transistors 418D, 418E and 418F.

Another storage node contact SNB couples together the drains of transistors 420D, 420E and 420F.

In some embodiments, SRAM cell 408 is a duplicate cell but, relative to an imaginary reference line 415 parallel to the X axis, is mirror symmetric with respect to SRAM cell 406. In some embodiments, the common features BL, VCC, and VSS, are combined to save space. Thus, the two cells pack into a space that is less than twice the cell boundary area. The N-wells are combined and extend in the Y direction, as do the P-wells.

Moreover, in FIG. 4B, in the p-well regions, continuous fins 410 and 414 are employed to form transistors and are correspondingly shared by adjacent SRAM cells 406 and 408. In contrast, in the n-well region, discontinuous fin segments 412A and 412B are employed to form transistors, with SRAM cell 406 using fin segment 412A and SRAM cell 408 using fin segment 412B. For example, transistor 418C of SRAM cell 406 uses fin segment 412A and transistor 420c of SRAM cell 408 uses fin segment 412B.

One of ordinary skill in the art would recognize that operations are able to be removed or that additional operations are able to be added to at least one of the above-noted methods without departing from the scope of this description. One of ordinary skill in the art would also recognize that an order of operations in at least one of the above-noted methods is able to be adjusted without departing from the scope of this description.

In some embodiments, a method (of manufacturing fins for a semiconductor device) includes: forming semiconductor fins including ones thereof having a first cap with a first etch sensitivity (first capped fins) and second ones thereof having a second cap with a second etch sensitivity (second capped fins), the first and second etch sensitivities being different; and eliminating selected ones of the first capped fins and selected ones of the second capped fins.

In some embodiments, the eliminating includes: removing second caps of selected ones of the second capped fins resulting in second uncapped fins; removing first caps of selected ones of the first capped fins resulting in first uncapped fins; and removing the first and second uncapped fins.

In some embodiments, the removing the second caps of the selected ones of the second capped fins includes: forming first masks over unselected ones of the second capped fins to leave the selected ones of the second capped fins exposed; etching the selected ones of the second capped fins with a second etchant appropriate for the second etch sensitivity to remove the second cap from each selected one of the second capped fins resulting in the second uncapped fins; and removing the first mask.

In some embodiments, the forming first masks includes: extending spans of the first masks to cover some of the first capped fins.

In some embodiments, the removing the first caps of the selected ones of the first capped fins includes: forming second masks over unselected ones of the first capped fins to leave the selected ones of the first capped fins exposed; etching the selected ones of the first capped fins with a first etchant appropriate for the first etch sensitivity to remove the first cap from each selected one of the first capped fins; and removing the second masks.

In some embodiments, the forming second masks includes extending spans of the second masks also to cover some of the second capped fins.

In some embodiments, before the forming semiconductor fins, the method further includes: forming a first layer on a semiconductor substrate, the first layer having interspersed first spacers and etch stop layer (ESL) portions; forming second spacers on corresponding first spacers and ESL portions; removing exposed regions of the first spacers and ESL portions and portions of the semiconductor substrate lying thereunder resulting in first and second precursors correspondingly of the first and second capped fins; and removing the second spacers resulting in the first capped fins and the second capped fins.

In some embodiments, the forming a first layer includes: building first mandrel features on the semiconductor substrate to leave first regions of the semiconductor substrate exposed; building, in some areas of the first regions, the first spacers on the semiconductor substrate, the first spacers abutting sidewalls of the first mandrel features to leave second regions of the semiconductor substrate exposed; removing the first mandrel features to leave third regions of the semiconductor substrate exposed; and forming, in the third regions, the ESL portions on the semiconductor substrate, the ESL portions abutting sidewalls of the first spacers.

In some embodiments, the forming second spacers on corresponding first spacers and ESL portions includes: building second mandrel features on areas of the first spacers and ESL portions to leave fourth regions of the first spacers and ESL portions exposed; building, in some areas of the fourth regions, third spacers so as to abut sidewalls of the second mandrel features and to leave fifth regions of the first spacers and ESL portions exposed; removing the second mandrel features to leave sixth regions of the first spacers and ESL portions exposed; building the second spacers on areas of the sixth regions so as to abut sidewalls of the third spacers and to leave seventh regions of the first spacers and ESL portions exposed; removing the third spacers to leave eighth regions of the first spacers and ESL portions exposed; and removing the exposed eighth regions of the first spacers and ESL portions and a portion of the semiconductor substrate lying thereunder resulting in the first and second precursors correspondingly of the first and second capped fins.

In some embodiments, relative to a cross section taken along a reference direction parallel to a plane of the semiconductor substrate: widths of the first spacers and ESL portions are the same; the first spacers and ESL portions are interleaved into a sequence of pairs; each pair includes a given one of the first spacers and a given one of the ESL portions; and the forming second spacers includes centering the second spacers over centers of the corresponding first spacers and ESL portions.

In some embodiments, before the forming semiconductor fins, the method further includes: forming a first layer on a semiconductor substrate, the first layer having interspersed first spacers, first etch stop layer (ESL) portions and second spacers such that, relative to a reference direction parallel to a plane of the semiconductor substrate, each second spacer abuts a corresponding one of the first spacers and a corresponding one of the first ESL portions, each first spacer abuts corresponding ones of the second spacers, and each first ESL portion abuts corresponding ones of the second spacers; forming second ESL portions correspondingly on the first spacers and the first ESL portions; removing the second spacers; removing exposed regions of the first spacers and ESL portions and portions of the semiconductor substrate lying thereunder resulting in first and second capped precursors correspondingly of the first and second capped fins; and removing the second ESL portions resulting in the first and second capped fins.

In some embodiments, the forming a first layer includes: building first mandrel features on the semiconductor substrate to leave first regions of the semiconductor substrate exposed; building, in some areas of the first regions, second spacers on the semiconductor substrate, the second spacers abutting sidewalls of the first mandrel features to leave second regions of the semiconductor substrate exposed; removing the first mandrel features to leave third regions of the semiconductor substrate exposed; building, in some areas of the third regions, the first spacers on the semiconductor substrate, the first spacers abutting sidewalls of the second spacers; removing the second spacers to leave fourth regions of the semiconductor substrate exposed; building, in some areas of the fourth regions, the second spacers on the semiconductor substrate, the second spacers abutting sidewalls of the first spacers to leave fifth regions of the semiconductor substrate exposed; and forming, in the fifth regions, the first ESL portions on the semiconductor substrate, the first ESL portions abutting sidewalls of the second spacers.

In some embodiments, the forming second ESL portions includes: removing portions of the first spacers and the first ESL portions thereby to shorten the first spacers and the first ESL portions resulting in gaps between the second spacers over the shortened first spacers and the shortened first ESL portions; depositing a layer of second etch-stop material on the second spacers, the shortened first spacers and the shortened first ESL portions; and removing a part of the layer of second etch-stop material to expose the second spacers.

In some embodiments, a method (of manufacturing fins for a semiconductor device) includes: forming semiconductor fins including ones thereof having a first cap with a first etch sensitivity (first capped fins) and second ones thereof having a second cap with a second etch sensitivity (second capped fins), the first and second etch sensitivities being different; removing second caps and first caps correspondingly of selected ones of the second capped fins and the first capped fins; resulting in second and first uncapped fins; and removing the first and second uncapped fins.

In some embodiments, before the forming semiconductor fins, the method further includes: forming a first layer on a semiconductor substrate, the first layer having interspersed first spacers and etch stop layer (ESL) portions; forming second spacers on corresponding first spacers and ESL portions; removing exposed regions of the first spacers and ESL portions and portions of the semiconductor substrate lying thereunder resulting in first and second precursors correspondingly of the first and second uncapped fins; and removing the second spacers resulting in the first capped fins and the second capped fins.

In some embodiments, relative to a cross section taken along a reference direction parallel to a plane of the semiconductor substrate: widths of the first spacers and ESL portions are the same; the first spacers and ESL portions are interleaved into a sequence of pairs; each pair includes a given one of the first spacers and a given one of the ESL portions; and the forming second spacers includes: centering the second spacers over centers of the corresponding first spacers and ESL portions.

In some embodiments, before the forming semiconductor fins, the method further includes: forming a first layer on a semiconductor substrate, the first layer having interspersed first spacers, first etch stop layer (ESL) portions and second spacers such that, relative to a reference direction parallel to a plane of the semiconductor substrate, each second spacer abuts a corresponding one of the first spacers and a corresponding one of the first ESL portions, each first spacer abuts corresponding ones of the second spacers, and each first ESL portion abuts corresponding ones of the second spacers; forming second ESL portions correspondingly on the first spacers and the first ESL portions; removing the second spacers; removing exposed regions of the first spacers and ESL portions and portions of the semiconductor substrate lying thereunder resulting in first and second precursors correspondingly of the first and second capped fins; and removing the second ESL portions resulting in the first and second capped fins.

In some embodiments, a method (of manufacturing fins for a semiconductor device) includes: forming semiconductor fins including ones thereof having a first cap with a first etch sensitivity (first capped fins) and second ones thereof having a second cap with a second etch sensitivity (second capped fins), the first and second etch sensitivities being different; forming first masks over unselected second capped fins so as to leave selected second capped fins exposed; etching with an etchant appropriate for the second etch resulting in second uncapped fins; removing the first mask; forming second masks over unselected ones of the first capped fins so as to leave selected first capped fins exposed; etching with an etchant appropriate for the first etch sensitivity resulting in first uncapped fins; and removing the second masks; and removing the first and second uncapped fins.

In some embodiments, before the forming semiconductor fins, the method further includes: forming a first layer on a semiconductor substrate, the first layer having interspersed first spacers and etch stop layer (ESL) portions; forming second spacers on corresponding first spacers and ESL portions; removing exposed regions of the first spacers and ESL portions and portions of the semiconductor substrate lying thereunder resulting in first and second precursors correspondingly of the first and second uncapped fins; and removing the second spacers resulting in the first capped fins and the second capped fins.

In some embodiments, before the forming semiconductor fins, the method further includes: forming a first layer on a semiconductor substrate, the first layer having interspersed first spacers, first etch stop layer (ESL) portions and second spacers such that, relative to a reference direction parallel to a plane of the semiconductor substrate, each second spacer abuts a corresponding one of the first spacers and a corresponding one of the first ESL portions, each first spacer abuts corresponding ones of the second spacers, and each first ESL portion abuts corresponding ones of the second spacers; forming second ESL portions correspondingly on the first spacers and the first ESL portions; removing the second spacers; removing exposed regions of the first spacers and ESL portions and portions of the semiconductor substrate lying thereunder resulting in first and second precursors correspondingly of the first and second capped fins; and removing the second ESL portions resulting in the first and second capped fins.

The foregoing outlines features of several embodiments so that those of ordinary skill in the art may better understand the aspects of the present disclosure. Those of ordinary skill in the art should appreciate that they may readily use the present disclosure as a basis for designing or modifying other circuits, processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. A method of manufacturing fins for a semiconductor device, the method comprising:
   forming semiconductor fins including ones thereof having a first cap with a first etch sensitivity (first capped fins) and second ones thereof having a second cap with a second etch sensitivity (second capped fins), the first and second etch sensitivities being different; and
   eliminating selected ones of the first capped fins and selected ones of the second capped fins.

2. The method of claim 1, wherein the eliminating includes:
   removing second caps of selected ones of the second capped fins resulting in second uncapped fins;
   removing first caps of selected ones of the first capped fins resulting in first uncapped fins; and
   removing the first and second uncapped fins.

3. The method of claim 2, wherein the removing the second caps of the selected ones of the second capped fins includes:
   forming first masks over unselected ones of the second capped fins to leave the selected ones of the second capped fins exposed;
   etching the selected ones of the second capped fins with a second etchant appropriate for the second etch sensitivity to remove the second cap from each selected one of the second capped fins resulting in the second uncapped fins; and
   removing the first mask.

4. The method of claim 3, wherein the forming first masks includes:
   extending spans of the first masks to cover some of the first capped fins.

5. The method of claim 2, wherein the removing the first caps of the selected ones of the first capped fins includes:
   forming second masks over unselected ones of the first capped fins to leave the selected ones of the first capped fins exposed;
   etching the selected ones of the first capped fins with a first etchant appropriate for the first etch sensitivity to remove the first cap from each selected one of the first capped fins; and
   removing the second masks.

6. The method of claim 5, wherein:
   the forming second masks includes:
      extending spans of the second masks also to cover some of the second capped fins.

7. The method of claim 1, wherein, before the forming semiconductor fins, the method further comprises:
   forming a first layer on a semiconductor substrate, the first layer having interspersed first spacers and etch stop layer (ESL) portions;
   forming second spacers on corresponding first spacers and ESL portions;
   removing exposed regions of the first spacers and ESL portions and portions of the semiconductor substrate lying thereunder resulting in first and second precursors correspondingly of the first and second capped fins; and
   removing the second spacers resulting in the first capped fins and the second capped fins.

8. The method of claim 7, wherein the forming a first layer includes:
   building first mandrel features on the semiconductor substrate to leave first regions of the semiconductor substrate exposed;

building, in some areas of the first regions, the first spacers on the semiconductor substrate, the first spacers abutting sidewalls of the first mandrel features to leave second regions of the semiconductor substrate exposed;

removing the first mandrel features to leave third regions of the semiconductor substrate exposed; and forming, in the third regions, the ESL portions on the semiconductor substrate, the ESL portions abutting sidewalls of the first spacers.

9. The method of claim 8, wherein the forming second spacers on corresponding first spacers and ESL portions includes:

building second mandrel features on areas of the first spacers and ESL portions to leave fourth regions of the first spacers and ESL portions exposed;

building, in some areas of the fourth regions, third spacers so as to abut sidewalls of the second mandrel features and to leave fifth regions of the first spacers and ESL portions exposed;

removing the second mandrel features to leave sixth regions of the first spacers and ESL portions exposed;

building the second spacers on areas of the sixth regions so as to abut sidewalls of the third spacers and to leave seventh regions of the first spacers and ESL portions exposed;

removing the third spacers to leave eighth regions of the first spacers and ESL portions exposed; and removing the exposed eighth regions of the first spacers and ESL portions and a portion of the semiconductor substrate lying thereunder resulting in the first and second precursors correspondingly of the first and second capped fins.

10. The method of claim 7, wherein, relative to a cross section taken along a reference direction parallel to a plane of the semiconductor substrate:

widths of the first spacers and ESL portions are the same;

the first spacers and ESL portions are interleaved into a sequence of pairs;

each pair includes a given one of the first spacers and a given one of the ESL portions; and the forming second spacers includes:

centering the second spacers over centers of the corresponding first spacers and ESL portions.

11. The method of claim 1, wherein, before the forming semiconductor fins, the method further comprises:

forming a first layer on a semiconductor substrate, the first layer having interspersed first spacers, first etch stop layer (ESL) portions and second spacers such that, relative to a reference direction parallel to a plane of the semiconductor substrate, each second spacer abuts a corresponding one of the first spacers and a corresponding one of the first ESL portions, each first spacer abuts corresponding ones of the second spacers, and each first ESL portion abuts corresponding ones of the second spacers;

forming second ESL portions correspondingly on the first spacers and the first ESL portions;

removing the second spacers;

removing exposed regions of the first spacers and ESL portions and portions of the semiconductor substrate lying thereunder resulting in first and second precursors correspondingly of the first and second capped fins; and removing the second ESL portions resulting in the first and second capped fins.

12. The method of claim 11, wherein the forming a first layer includes:

building first mandrel features on the semiconductor substrate to leave first regions of the semiconductor substrate exposed;

building, in some areas of the first regions, second spacers on the semiconductor substrate, the second spacers abutting sidewalls of the first mandrel features to leave second regions of the semiconductor substrate exposed;

removing the first mandrel features to leave third regions of the semiconductor substrate exposed;

building, in some areas of the third regions, the first spacers on the semiconductor substrate, the first spacers abutting sidewalls of the second spacers;

removing the second spacers to leave fourth regions of the semiconductor substrate exposed;

building, in some areas of the fourth regions, the second spacers on the semiconductor substrate, the second spacers abutting sidewalls of the first spacers to leave fifth regions of the semiconductor substrate exposed; and forming, in the fifth regions, the first ESL portions on the semiconductor substrate, the first ESL portions abutting sidewalls of the second spacers.

13. The method of claim 12, wherein the forming second ESL portions includes:

removing portions of the first spacers and the first ESL portions thereby to shorten the first spacers and the first ESL portions resulting in gaps between the second spacers over the shortened first spacers and the shortened first ESL portions;

depositing a layer of second etch-stop material on the second spacers, the shortened first spacers and the shortened first ESL portions; and removing a part of the layer of second etch-stop material to expose the second spacers.

14. A method of manufacturing fins for a semiconductor device, the method comprising:

forming semiconductor fins including ones thereof having a first cap with a first etch sensitivity (first capped fins) and second ones thereof having a second cap with a second etch sensitivity (second capped fins), the first and second etch sensitivities being different;

removing second caps and first caps correspondingly of selected ones of the second capped fins and the first capped fins; resulting in second and first uncapped fins; and removing the first and second uncapped fins.

15. The method of claim 14, wherein, before the forming semiconductor fins, the method further comprises:

forming a first layer on a semiconductor substrate, the first layer having interspersed first spacers and etch stop layer (ESL) portions;

forming second spacers on corresponding first spacers and ESL portions;

removing exposed regions of the first spacers and ESL portions and portions of the semiconductor substrate lying thereunder resulting in first and second precursors correspondingly of the first and second uncapped fins; and removing the second spacers resulting in the first capped fins and the second capped fins.

16. The method of claim 15, wherein, relative to a cross section taken along a reference direction parallel to a plane of the semiconductor substrate:

widths of the first spacers and ESL portions are the same;

the first spacers and ESL portions are interleaved into a sequence of pairs;

each pair includes a given one of the first spacers and a given one of the ESL portions; and the forming second spacers includes:

centering the second spacers over centers of the corresponding first spacers and ESL portions.

17. The method of claim 14, wherein, before the forming semiconductor fins, the method further comprises:

forming a first layer on a semiconductor substrate, the first layer having interspersed first spacers, first etch stop layer (ESL) portions and second spacers such that, relative to a reference direction parallel to a plane of the semiconductor substrate, each second spacer abuts a corresponding one of the first spacers and a corresponding one of the first ESL portions, each first spacer abuts corresponding ones of the second spacers, and each first ESL portion abuts corresponding ones of the second spacers;

forming second ESL portions correspondingly on the first spacers and the first ESL portions;

removing the second spacers;

removing exposed regions of the first spacers and ESL portions and portions of the semiconductor substrate lying thereunder resulting in first and second precursors correspondingly of the first and second capped fins; and removing the second ESL portions resulting in the first and second capped fins.

18. A method of manufacturing fins for a semiconductor device, the method comprising:

forming semiconductor fins including ones thereof having a first cap with a first etch sensitivity (first capped fins) and second ones thereof having a second cap with a second etch sensitivity (second capped fins), the first and second etch sensitivities being different;

forming first masks over unselected second capped fins so as to leave selected second capped fins exposed;

etching with an etchant appropriate for the second etch resulting in second uncapped fins;

removing the first mask;

forming second masks over unselected ones of the first capped fins so as to leave selected first capped fins exposed;

etching with an etchant appropriate for the first etch sensitivity resulting in first uncapped fins; and removing the second masks; and removing the first and second uncapped fins.

19. The method of claim 18, wherein, before the forming semiconductor fins, the method further comprises:

forming a first layer on a semiconductor substrate, the first layer having interspersed first spacers and etch stop layer (ESL) portions;

forming second spacers on corresponding first spacers and ESL portions;

removing exposed regions of the first spacers and ESL portions and portions of the semiconductor substrate lying thereunder resulting in first and second precursors correspondingly of the first and second uncapped fins; and removing the second spacers resulting in the first capped fins and the second capped fins.

20. The method of claim 18, wherein, before the forming semiconductor fins, the method further comprises:

forming a first layer on a semiconductor substrate, the first layer having interspersed first spacers, first etch stop layer (ESL) portions and second spacers such that, relative to a reference direction parallel to a plane of the semiconductor substrate, each second spacer abuts a corresponding one of the first spacers and a corresponding one of the first ESL portions, each first spacer abuts corresponding ones of the second spacers, and each first ESL portion abuts corresponding ones of the second spacers;

forming second ESL portions correspondingly on the first spacers and the first ESL portions;

removing the second spacers;

removing exposed regions of the first spacers and ESL portions and portions of the semiconductor substrate lying thereunder resulting in first and second precursors correspondingly of the first and second capped fins; and removing the second ESL portions resulting in the first and second capped fins.

* * * * *